United States Patent
Lin et al.

(10) Patent No.: US 11,898,061 B2
(45) Date of Patent: Feb. 13, 2024

(54) MODIFIED CONDUCTIVE STRUCTURE AND METHOD FOR PRODUCING THE SAME

(71) Applicant: Industrial Technology Research Institute, Hsinchu (TW)

(72) Inventors: Hsin-Chieh Lin, Taoyuan (TW); Chih Chang, Taichung (TW); Chin Pen Lai, Minxiong Township (TW); Wang-Chin Cheng, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 890 days.

(21) Appl. No.: 16/658,589

(22) Filed: Oct. 21, 2019

(65) Prior Publication Data

US 2020/0157360 A1    May 21, 2020

Related U.S. Application Data

(60) Provisional application No. 62/754,833, filed on Nov. 2, 2018.

(51) Int. Cl.
C09D 5/16 (2006.01)
H01B 1/12 (2006.01)
(Continued)

(52) U.S. Cl.
CPC ........ *C09D 5/1662* (2013.01); *A61B 5/14532* (2013.01); *A61B 5/14865* (2013.01);
(Continued)

(58) Field of Classification Search
CPC .................................................. C09D 5/1662
See application file for complete search history.

(56) References Cited

U.S. PATENT DOCUMENTS 9,695,275 B2    7/2017    Cheng
9,714,912 B2    7/2017    Choudhary et al.
(Continued)

FOREIGN PATENT DOCUMENTS

EP    2840144 A1    2/2015
TW    I360231 B    3/2012
(Continued)

OTHER PUBLICATIONS

Taiwanese Office Action and Search Report for Taiwanese Application No. 108137840, dated Nov. 19, 2020.
(Continued)

*Primary Examiner* — William D Young
(74) *Attorney, Agent, or Firm* — Birch, Stewart, Kolasch & Birch, LLP

(57) ABSTRACT

A modified conductive structure includes a conductive substrate and a polymer film disposed over a surface of the
(Continued)

10 polymer film. A chemical bond exists between the polymer film and the conductive substrate, and the polymer film includes repeating units as shown below:

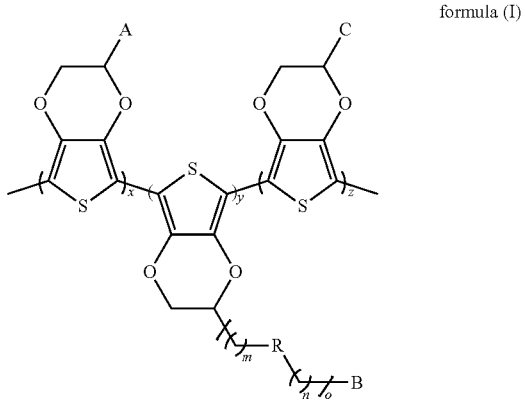

formula (I)

wherein A is an antifouling molecule group; B is a sulfur-containing group or a nitrogen-containing group; R is a single bond or a first linking group; C is -L-E, wherein L is a second linking group, E is an enzyme unit; x and z are each independently 0 or an integer from 1 to 10000, and y is an integer from 1 to 10000; o is 0 or an integer from 1 to 50, and when o is an integer from 1 to 50, m and n are each independently 0 or an integer from 1 to 50.

14 Claims, 17 Drawing Sheets

(51) Int. Cl.
| | | |
|---|---|---|
| C08G 61/12 | (2006.01) | |
| C09D 165/00 | (2006.01) | |
| C09D 5/24 | (2006.01) | |
| C12Q 1/00 | (2006.01) | |
| A61B 5/1486 | (2006.01) | |
| A61B 5/145 | (2006.01) | |
| A61N 1/05 | (2006.01) | |
| C25D 9/02 | (2006.01) | |
| H01B 5/00 | (2006.01) | |

(52) U.S. Cl.
CPC ............. *A61N 1/05* (2013.01); *C08G 61/126* (2013.01); *C09D 5/24* (2013.01); *C09D 165/00* (2013.01); *C12Q 1/005* (2013.01); *C25D 9/02* (2013.01); *H01B 1/127* (2013.01); *H01B 5/002* (2013.01); *C08G 2261/1424* (2013.01); *C08G 2261/3223* (2013.01); *C08G 2261/344* (2013.01); *C08G 2261/51* (2013.01); *C08G 2261/94* (2013.01)

(56) References Cited

U.S. PATENT DOCUMENTS

| 9,743,870 B2 | 8/2017 | Wang et al. |
| 9,755,390 B2 | 9/2017 | Hanssen et al. |
| 9,869,652 B2 | 1/2018 | Rozlosnik et al. |
| 9,883,826 B2 | 2/2018 | Jamieson et al. |
| 9,890,467 B2 | 2/2018 | Richardson-Burns et al. |
| 9,952,197 B2 | 4/2018 | Saeda et al. |
| 2014/0011004 A1 | 1/2014 | Sotzing et al. |
| 2016/0208114 A1 | 7/2016 | Hendricks et al. |
| 2016/0244554 A1* | 8/2016 | Cheng ............... A61L 27/18 |
| 2017/0027481 A1 | 2/2017 | Coppede' et al. |
| 2018/0282472 A1* | 10/2018 | Cheng ............... C25D 9/02 |

FOREIGN PATENT DOCUMENTS

| TW | I366246 B | 6/2012 |
| TW | 201311862 A1 | 3/2013 |
| TW | 201326251 A1 | 7/2013 |
| TW | 201734149 A | 10/2017 |
| TW | 201833280 A | 9/2018 |
| WO | WO 2015/054484 A1 | 4/2015 |
| WO | WO 2015/095758 A1 | 6/2015 |
| WO | WO 2017/058871 A1 | 4/2017 |

OTHER PUBLICATIONS

Turkarslan, et al., "Poly(pyrrole) versus poly(3,4-ethylenedioxythiophene): amperometric cholesterol biosensor matrices", J. Solid State Electrochem, 2009, vol. 13, pp. 657-663.

Zhao, et al., "Glucose Sensing by Glucose Oxidase/PEDOT Thin Film Electrode", Molecular Crystals and Liquid Crystals, 2013, vol. 580, pp. 22-28.

Zhu, et al., "Large enhancement in neurite outgrowth on a cell membrane-mimicking conducting polymer", Nature Communications, 2014, vol. 5:4523, pp. 1-9.

\* cited by examiner

10

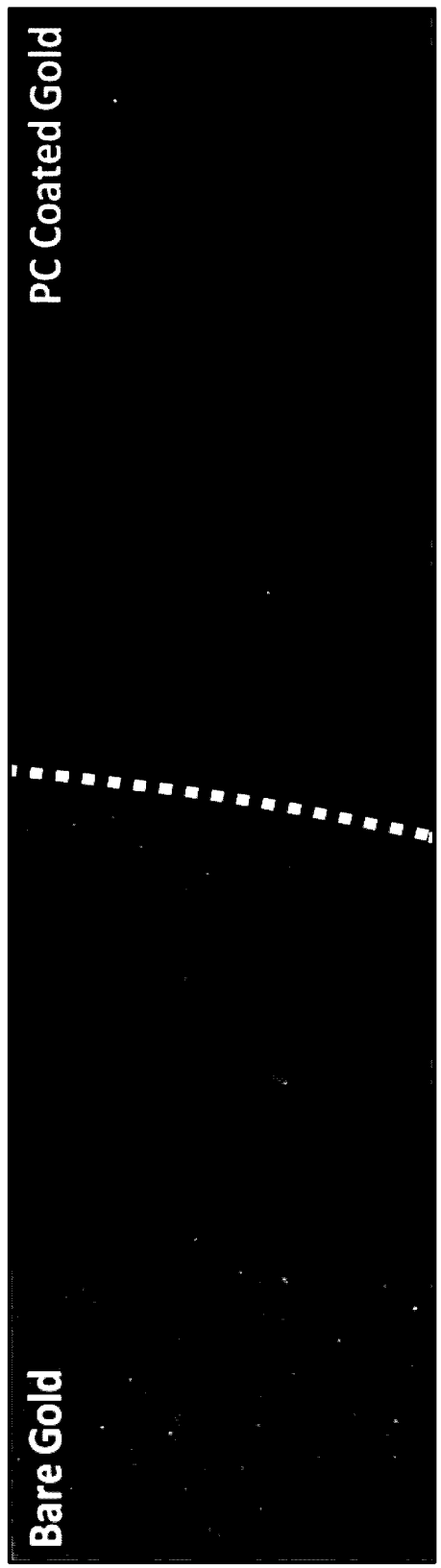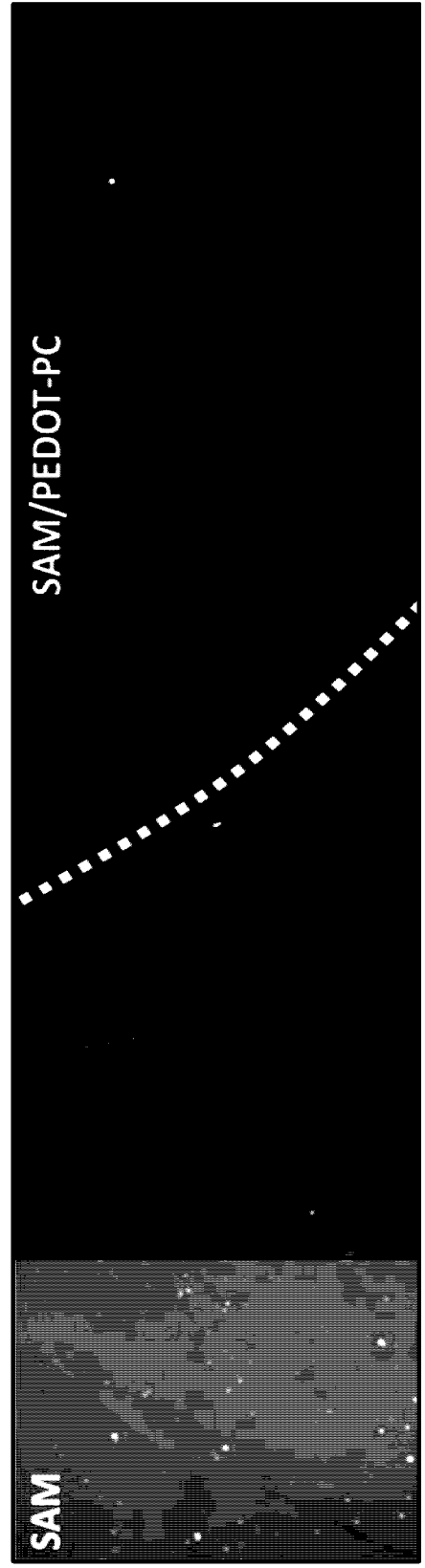
FIG. 5A
FIG. 5B

FIG. 11A
FIG. 11B
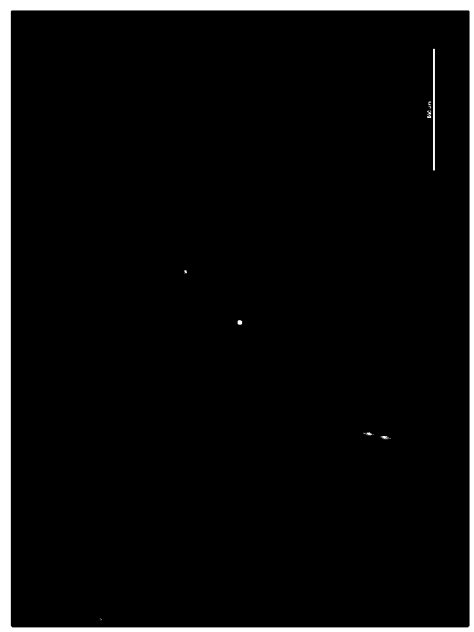
FIG. 11C
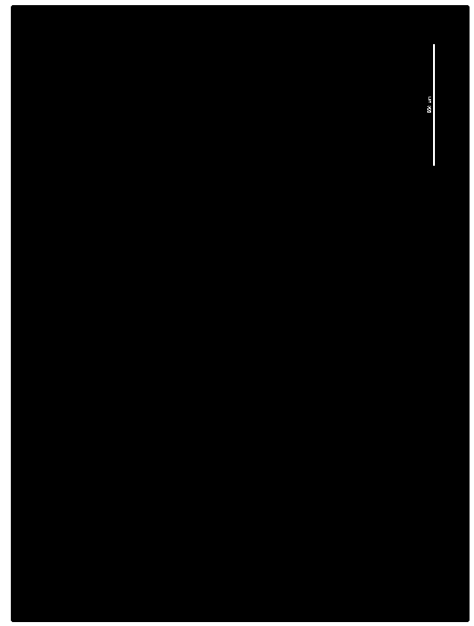
FIG. 11D

MODIFIED CONDUCTIVE STRUCTURE AND METHOD FOR PRODUCING THE SAME

CROSS REFERENCE TO RELATED APPLICATIONS

This application claims priority of U.S. Provisional Patent Application No. 62/754,833, filed on Nov. 2, 2018, the entirety of which is incorporated by reference herein.

TECHNICAL FIELD

The present disclosure relates to a modified conductive structure and a method for producing the same, and in particular it relates to a conductive structure modified with a polymer film and a method for producing the same.

BACKGROUND

In recent years, implantable devices have flourished in the biomedical field, and the global market for implantable medical devices has also grown rapidly. Implantable medical devices can be used in clinical applications to diagnose epidemic diseases, detect early-stage cancers, and monitor chronic diseases in the long term. Generally, probes made of metal materials are often used to convert biological signals in the body into readable signals. Among them, gold and platinum have high conductivity, ductility, biocompatibility, and corrosion resistance, and therefore they are considered suitable materials for producing probes or electrodes for in vivo detection.

However, biofouling and biological adhesion issues can occur easily due to the contact of implantable devices with tissues in the body, which may cause a malfunction or dysfunction of the implanted devices. In order to prolong the service life of the implantable devices and improve their performance, demand for anti-nonspecific biological adhesion ability of the device surface (especially the surface of the conductive structure) is increasing.

The methods that are commonly used include decorating and modifying the surface of the probe electrode with a modification material to improve the anti-biofouling ability. The modification methods are mainly physical modifications, e.g., the modification materials are physically attached to the surface of the probe electrode. However, the impedance is high, and the modification materials are easy to fall off with time, which may not only cause health concerns for patients but gradually decrease the signal sensitivity. Therefore, the probe electrode that is modified with such a manner may be not suitable for long-term biomedical detection applications.

As described above, although currently existing conductive structures for implantable devices have been substantially adequate for their intended purposes, they have not been satisfactory in the needs of long-term implantation.

SUMMARY

In accordance with some embodiments of the present disclosure, a modified conductive structure is provided. The modified conductive structure comprises a conductive substrate and a polymer film disposed over a surface of the polymer film. A chemical bond exists between the polymer film and the conductive substrate. The polymer film comprises repeating units as shown below:

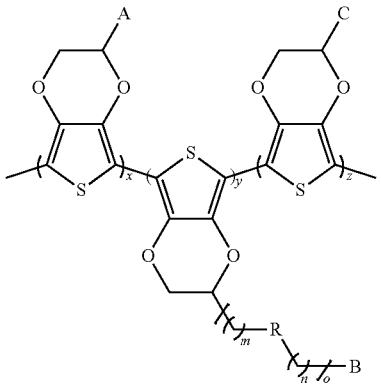

formula (I)

wherein A is an antifouling molecule group; B is a sulfur-containing group or a nitrogen-containing group; R is a single bond or a first linking group; C is -L-E, wherein L is a second linking group, E is an enzyme unit; x and z are each independently 0 or an integer from 1 to 10000, and y is an integer from 1 to 10000; o is 0 or an integer from 1 to 50, and when o is an integer from 1 to 50, m and n are each independently 0 or an integer from 1 to 50.

In accordance with some embodiments of the present disclosure, a method for producing a modified conductive structure is provided. The method comprises: providing a conductive substrate; forming a self-assembly monolayer on a surface of the conductive substrate using a first monomer shown as formula (II) below, and a chemical bond existing between the self-assembly monolayer and the surface of the conductive substrate; and providing a monomer composition, wherein the monomer composition and the self-assembly monolayer are subjected to a polymerization reaction to form a polymer film.

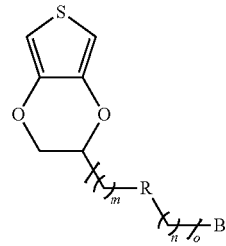

formula (II)

In formula (II), B is a sulfur-containing group or a nitrogen-containing group; R is a single bond or a first linking group; o is 0 or an integer from 1 to 50, and when o is an integer from 1 to 50, m and n are each independently 0 or an integer from 1 to 50. In addition, the monomer composition comprises a first monomer, a second monomer, a third monomer or a combination thereof.

In order to make the features or advantages of the present disclosure more obvious and easy to understand, a detailed description is given in the following embodiments with reference to the accompanying drawings.

BRIEF DESCRIPTION OF DRAWINGS

FIGS. 5A and 5B show test results of the anti-protein adhesion ability of the conductive structures in some Examples and Comparative Examples of the present disclosure;

FIGS. 11A to 11D show test results of the anti-cell adhesion ability of the conductive structures in some Examples and Comparative Examples of the present disclosure;

DETAILED DESCRIPTION

Figure 1:
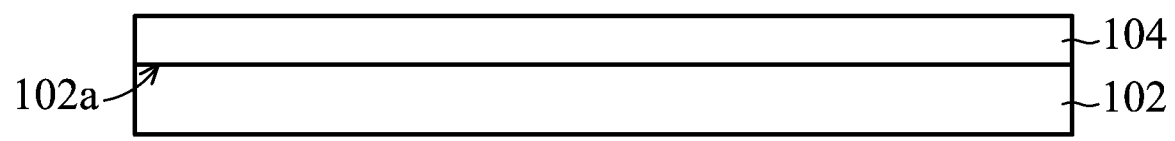
FIG. 1 is a structural diagram of the modified conductive structure in accordance with some embodiments of the present disclosure.

The modified conductive structure of the present disclosure and the method for producing the same are described in detail in the following description. It should be understood that in the following detailed description, for purposes of explanation, numerous specific details and embodiments are set forth in order to provide a thorough understanding of the present disclosure. The specific elements and configurations described in the following detailed description are set forth in order to clearly describe the present disclosure. However, it will be apparent that the exemplary embodiments set forth herein are used merely for the purpose of illustration, and the concept of the present disclosure may be embodied in various forms without being limited to those exemplary embodiments. In addition, the drawings of different embodiments may use repeated numerals to denote the elements. However, the use of repeated numerals in the drawings of different embodiments does not suggest any correlation between different embodiments and/or structures.

In addition, it should be understood that although the terms "first", "second", "third" etc. may be used herein to describe various elements, components, regions, layers, portions and/or sections, these elements, components, regions, layers, portions and/or sections should not be limited by these terms. These terms are only used to distinguish one element, component, region, layer, portion or section from another element, component, region, layer or section. Thus, a first element, component, region, layer, portion or section discussed below could be termed a second element, component, region, layer, portion or section without departing from the teachings of the present disclosure.

The description of the exemplary embodiments is intended to be read in connection with the accompanying drawings, which are to be considered part of the entire written description. It should be understood that the drawings are not drawn to scale. In fact, elements may be arbitrarily enlarged or reduced so that the features of the present disclosure can be clearly expressed. In addition, structures and devices are shown schematically in order to simplify the drawing.

The terms "about", "approximately" and "substantially" typically mean +/−20% of the stated value, more typically mean +/−10% of the stated value, more typically +/−5% of the stated value, or +/−3% of the stated value, or +/−2% of the stated value, or +/−1% of the stated value, or +/−0.5% of the stated value. The stated value of the present disclosure is an approximate value. When there is no specific description, the stated value includes the meaning of "about", "approximately" or "substantially".

In addition, the term "from the first value to the second value" means that the range includes the first value, the second value, and other values therebetween.

Unless defined otherwise, all technical and scientific terms used herein have the same meaning as commonly understood by one of ordinary skill in the art to which this disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

In accordance with some embodiments of the present disclosure, a modified conductive structure is provided. The modified conductive structure comprises a conductive substrate and a polymer film disposed over a surface of the conductive substrate, and a chemical bond exists between the polymer film and the conductive substrate. The polymer film comprises repeating units as shown below:

formula (I)

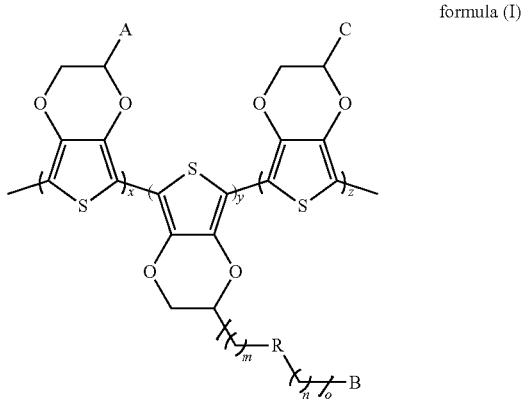

wherein A may be an antifouling molecule group; B may be a sulfur-containing group or a nitrogen-containing group; R may be a single bond or a first linking group; C may be -L-E, wherein L may be a second linking group, E may be an enzyme unit; x and z each may be independently 0 or an integer from 1 to 10000, and y may be an integer from 1 to 10000; o may be 0 or an integer from 1 to 50, and when o is an integer from 1 to 50, m and n each may be independently 0 or an integer from 1 to 50.

In some embodiments, in the conductive structure that is modified with the polymer film, the polymer film may be formed by the polymerization of specific conductive polymer monomers based on the self-assembly monolayer (SAM). The conductive polymer film having good conductivity, anti-biofouling ability and/or enzyme sensing function.

Refer to FIG. 1, which is a structural diagram of a modified conductive structure 10 in accordance with some embodiments of the present disclosure. It should be understood that additional features may be added to the modified conductive structure 10 in accordance with some embodiments of the present disclosure. As shown in FIG. 1, the modified conductive structure 10 may include a conductive substrate 102 and a polymer film 104 that is formed over a surface 102a of the conductive substrate 102. In addition, a chemical bond exists between the polymer film 104 and the conductive substrate 102. In some embodiments, the polymer film 104 is connected to the conductive substrate 102 via covalent bonds. In some embodiments, the modified conductive structure 10 may serve as an electrode.

The material of the conductive substrate 102 may include a conductive material, a semiconductor material, or a combination thereof. In some embodiments, the conductive material of the conductive substrate 102 may include a metallic material, such as gold (Au), platinum (Pt), aluminum (Al), iridium (Ir), titanium (Ti), steel, stainless steel, gold alloy, platinum alloy, platinum alloy, aluminum alloy, iridium alloy, titanium alloy, or a combination thereof, but it is not limited thereto. In some embodiments, the conductive material of the conductive substrate 102 may include a non-metallic material, such as a conductive oxide, a carbon material, or a combination thereof. For example, the conductive oxide may include, but is not limited to, indium tin oxide (ITO), fluorine-doped tin oxide (FTO), tin oxide (SnO), indium zinc oxide (IZO), indium gallium zinc oxide (IGZO), indium tin zinc oxide (ITZO), other suitable conductive oxides, or a combination thereof. The carbon material may include conductive graphite, carbon black, carbon nanotubes, graphene, or a combination thereof. In some embodiments, the carbon material may be a composite material. Furthermore, the semiconductor material may include silicon (Si). In some embodiments, the conductive substrate 102 may be a bulk formed of a semiconductor material. In some embodiments, the conductive substrate 102 may include a semiconductor material having a conductive material on its surface.

In some embodiments, the polymer film 104 may include repeating units shown as formula (I) below:

formula (I)

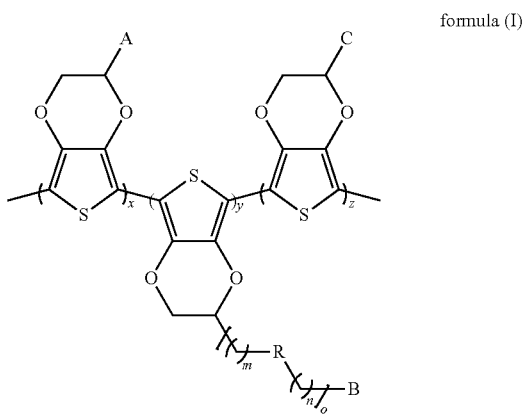

wherein A may be an antifouling molecule group; B may be a sulfur-containing group or a nitrogen-containing group; R may be a single bond or a first linking group; C may be -L-E, wherein L may be a second linking group, E may be an enzyme unit; x and z each may be independently 0 or an integer from 1 to 10000, and y may be an integer from 1 to 10000; o may be 0 or an integer from 1 to 50, and when o is an integer from 1 to 50, m and n each may be independently 0 or an integer from 1 to 50.

The polymer film 104 may be mainly formed of conductive polymer monomer derivatives. As shown in formula (I), the polymer film 104 may be polymerized mainly from derivatives of 3,4-ethylenedioxythiophene (EDOT), and the polymer formed thereof is known to have good biocompatibility and it is not easy to induce immune inflammatory response. In accordance with some embodiments, x and z may be each independently 0 or an integer from 1 to 10000, e.g., an integer from 1 to 5000, and y may be an integer from 1 to 10000, e.g., an integer from 1 to 1000. Specifically, in some embodiments, x and z may be 0, and y may be an integer from 1 to 5000. In some embodiments, z may be 0, x may be not 0, and x may be an integer from 1 to 5000. In some embodiments, x may be 0, z may be not 0, and z may be an integer from 1 to 1000.

In formula (I), B may be a group capable of forming a covalent bond with the conductive substrate 102, and B may also be referred to as an anchor group. As described above, in accordance with some embodiments, B may be a sulfur-containing group, for example, may have a disulfide bond. The disulfide bond may be reduced to a thiol group in a suitable environment, such that the repeating unit as shown in formula (I) may form a covalent bond with the surface 102a of the conductive substrate 102. Alternatively, in accordance with some embodiments, B may be a nitrogen-containing group, for example, may have an aniline group. The aniline group may form a covalent bond with the surface 102a of the conductive substrate 102 to enhance the stability of the modified polymer film 104 on the surface. More specifically, in accordance with some embodiments, B may be 1,2-dithiolane, thiol, aniline, diazonium salt, or a combination thereof.

As described above, in accordance with some embodiments, R may be a single bond. That is, B may be connected to 3,4-ethylenedioxythiophene through a linear alkyl group, for example, a $C_2$-$C_{50}$ linear alkyl group. In some embodiments, B may be connected to 3,4-ethylenedioxythiophene through ethyl, propyl, n-butyl, n-pentyl, n-hexyl, n-heptyl, or n-octyl.

In accordance with some embodiments, R may be the first linking group. That is, B may be connected to 3,4-ethylenedioxythiophene through the additional first linking group. In some embodiments, the first linking group may be ester, amide, thioester, ether, amine, ketone, sulfide, carbonate, carbamate, or a combination thereof.

In addition, in accordance with some embodiments, in the formula (I), o may be greater than 1, and a plurality of R may be the same or different from each other, or partially the same and partially different. In other words, —$(CH_2)_m$—, —R—, and —$(CH_2)_n$— may be randomly and repeatedly arranged and the repeated Rs may have the same or different structures.

Moreover, in formula (I), A may be the antifouling molecule group, which may reduce the anti-biofouling ability of the polymer film 104. In some embodiments, A may be a group having zwitterionic properties. In accordance with some embodiments, A may be betaine, amino acid, peptide, a polymer of 2-hydroxyethyl methacrylate (HEMA) or a derivative thereof, polyethylene glycol or an oligomer thereof (PEG or OEG), hydroxyl group, or a combination thereof.

In some embodiments, the betaine may include, but is not limited to, phosphobetaine (PB), sulfobetaine (SB), carboxybetaine (CB), or a combination thereof. In some embodiments, the amino acid may include, but is not limited to, cysteine (Cys), aspartic acid (Asp), glutamic acid (Glu), lysine (Lys), or a combination thereof. In some embodiments, the peptide may include 1 to 20 amino acids or 1 to 12 amino acids. In some embodiments, the structure of the peptide may include Asp-Cys, Glu-Cys, Cys-Lys, Cys-Lys-Cys-Lys, or a combination thereof, but it is not limited thereto.

Furthermore, in formula (I), C may be the enzyme group that can be connected to or form a bond with 3,4-ethylenedioxythiophene. As described above, C is -L-E, wherein L is the second linking group and E is the enzyme unit. That is, the enzyme unit may be connected to 3,4-ethylenedioxythiophene through the second linking group. The second linking group may be a group capable of forming a chemical bond with the enzyme to achieve the purpose of fixing the enzyme. In accordance with some embodiments, the second linking group may include a derivative of carbonyl or carboxylic acid. For example, in some embodiments, the second linking group may include, but is not limited to, maleimide (MI), acrylate, methacrylate, or a combination thereof.

In some embodiments, the enzyme unit may include, but is not limited to, glucose oxidase, glucose dehydrogenase, pyrroloquinoline quinine glucose dehydrogenase A (PQQGDH-A), pyrroquinoline quinone glucose dehydrogenase B (PQQGDH-B), NAD (P)-dependent glutamate dehydrogenase (NAD(P)-GDH), FAD-dependent glutamate dehydrogenase (FADGDH), uricase, urate oxidase, cholesterol oxidase, sulfur-containing enzyme, or a combination thereof. In some other embodiments, an enzyme unit having a suitable function may be selected according to the purpose of the polymer film 104.

Next, refer to FIG. 2A, and FIGS. 2A to 2D are structural diagrams of the modified conductive structure 10 during the producing processes in accordance with some embodiments of the present disclosure. It should be understood that, in some embodiments, additional operations may be provided before, during, and/or after the method for producing the modified conductive structure 10. In some embodiments, some of the operations described may be replaced or omitted according to need. In some embodiments, the order of operations/steps may be interchangeable.

Figure 2A:
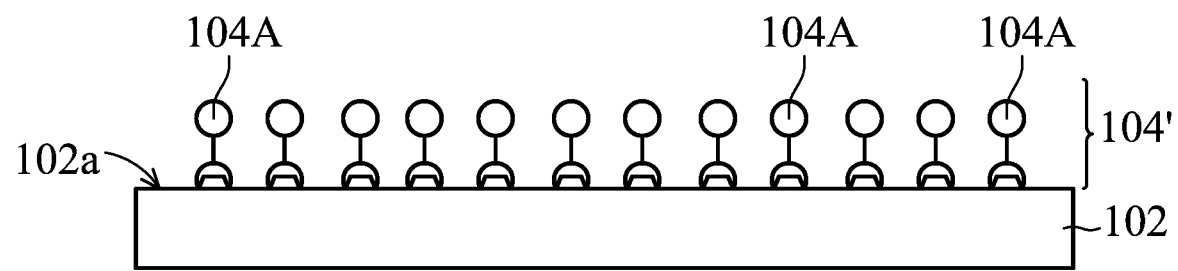
FIGS. 2A to 2D are structural diagrams of the modified conductive structure during the producing processes in accordance with some embodiments of the present disclosure.

First, referring to FIG. 2A, a conductive substrate 102 may be provided. The material of the conductive substrate 102 may include a conductive material, a semiconductor material, or a combination thereof. In some embodiments, the conductive material of the conductive substrate 102 may include a metallic material, such as gold (Au), platinum (Pt), aluminum (Al), iridium (Ir), titanium (Ti), steel, stainless steel, gold alloy, platinum alloy, platinum alloy, aluminum alloy, iridium alloy, titanium alloy or a combination thereof, but it is not limited thereto. In some embodiments, the conductive material of the conductive substrate 102 may include a non-metallic material, such as a conductive oxide, a carbon material, or a combination thereof. For example, the conductive oxide may include, but is not limited to, indium tin oxide (ITO), fluorine-doped tin oxide (FTO), tin oxide (SnO), indium zinc oxide (IZO), indium gallium zinc oxide (IGZO), indium tin zinc oxide (ITZO), other suitable conductive oxides, or a combination thereof. The carbon material may include conductive graphite, carbon black, carbon nanotubes, graphene, or a combination thereof. In some embodiments, the carbon material may be a composite material. Furthermore, the semiconductor material may include silicon (Si). In some embodiments, the conductive substrate 102 may be a bulk formed of a semiconductor material. In some embodiments, the conductive substrate 102 may include a semiconductor material having a conductive material on its surface.

Next, a self-assembly monolayer (SAM) 104' may be formed on the surface 102a of the conductive substrate 102 using a first monomer 104A shown in formula (II),

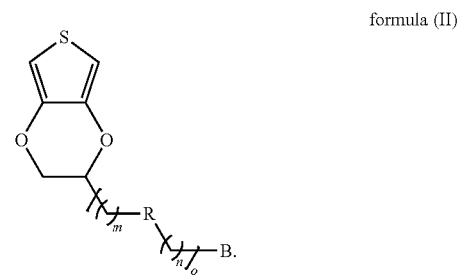

formula (II)

In formula (II), B may be a sulfur-containing group or a nitrogen-containing group; R may be a single bond or a first linking group; o may be 0 or an integer from 1 to 50, and when o is an integer from 1 to 50, M and n each may be independently 0 or an integer from 1 to 50. In addition, a chemical bond may exist between the self-assembly monolayer 104' and the surface 102a of the conductive substrate 102. In some embodiments, the self-assembly monolayer 104' may be connected to the conductive substrate 102 by forming a covalent bond between B in formula (II) with the conductive substrate 102.

In accordance with some embodiments, the conductive structure 10 may be based on the self-assembly monolayer 104' to form a polymer film 104 on the conductive substrate 102. In some embodiments, the first monomer 104A present in the liquid solution may spontaneously form the self-assembly film layer on the surface of the solid conductive substrate 102.

As described above, the first monomer 104A may be a derivative of 3,4-ethylenedioxythiophene (EDOT). In some embodiments, the first monomer 104A may be a derivative of 3,4-ethylenedioxythiophene (EDOT) and have an anchor group. In accordance with some embodiments, in formula (II), B may be a sulfur-containing group, for example, may have a disulfide bond. The disulfide bond may be reduced to a thiol group in a suitable environment, such that it may form a covalent bond with the surface 102a of the conductive substrate 102, thereby forming the self-assembly monolayer 104'. Alternatively, in accordance with some embodiments, in formula (II), B may be a nitrogen-containing group, for example, may have an aniline group. The aniline group may form a covalent bond with the surface 102a of the conductive substrate 102, thereby forming the self-assembly monolayer 104'. More specifically, in accordance with some embodiments, B may be 1,2-dithiolane, thiol, aniline, diazonium salt, or a combination thereof.

In accordance with some embodiments, in Formula (II), R may be a single bond. That is, B may be connected to 3,4-ethylenedioxythiophene through a linear alkyl group, for example, a $C_2$-$C_{50}$ linear alkyl group. In some embodiments, B may be connected to 3,4-ethylenedioxythiophene through ethyl, propyl, n-butyl, n-pentyl, n-hexyl, n-heptyl, or n-octyl.

In accordance with some embodiments, in formula (II), R may be a first linking group. That is, B may be connected to 3,4-ethylenedioxythiophene through the additional first linking group. In some embodiments, the first linking group may be ester, amide, thioester, ether, amine, ketone, sulfide, carbonate, carbamate, or a combination thereof.

In addition, in accordance with some embodiments, in the formula (II), o may be greater than 1, and a plurality of R may be the same or different from each other, or partially the same and partially different. In other words, —$(CH_2)_m$—, —R—, and —$(CH_2)_n$— may be randomly and repeatedly arranged and the repeated Rs may have the same or different structures.

In addition, in some embodiments, before the first monomers 104A form the self-assembly monolayer 104' on the surface 102a of the conductive substrate 102, a cleaning treatment and/or an activation treatment may be performed on the conductive substrate 102. In some embodiments, the cleaning and/or activation treatment may be performed using a chemical solution, ultraviolet ozone (UV ozone), a plasma process, a corona process, or a combination thereof. For example, in some embodiments, before the formation of the self-assembly monolayer 104', the conductive substrate 102 may be washed with a cleaning solution containing deionized water, ammonia water, and hydrogen peroxide water to remove organic pollutants or impurity particles on its surface.

In some embodiments, the self-assembly monolayer 104' may be formed on the conductive substrate 102 by an immersion (or soaking) process, a spraying process, a dispensing process, a printing process, or a combination thereof.

Figure 2B:
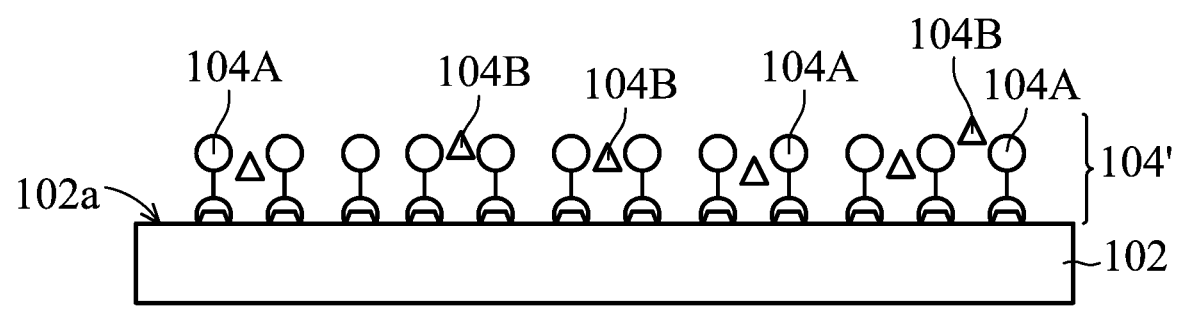
Figure 2C:
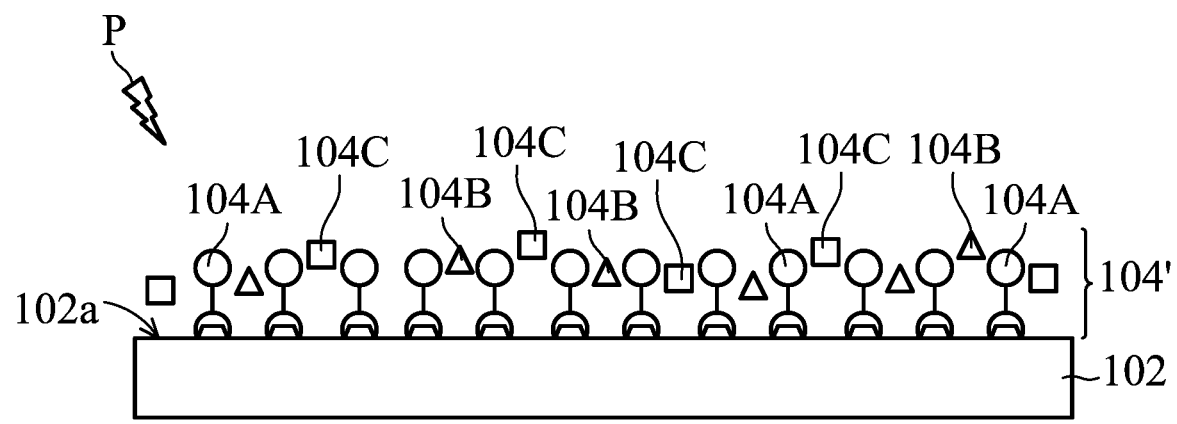
Figure 2D:
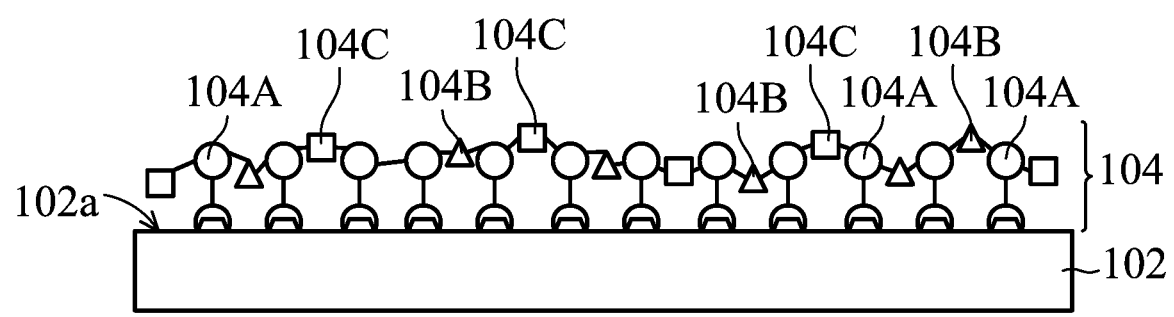

Next, a monomer composition may be provided, and the monomer composition and the self-assembly monolayer 104' may be subjected to a polymerization reaction P (sequentially as shown in FIGS. 2B, 2C and 2D) to form the polymer film 104. In accordance with some embodiments, the monomer composition may include a first monomer 104A, a second monomer 104B, a third monomer 104C, or a combination thereof.

As shown in FIG. 2B, in accordance with some embodiments, the monomer composition may include the second monomer 104B as shown in formula (III),

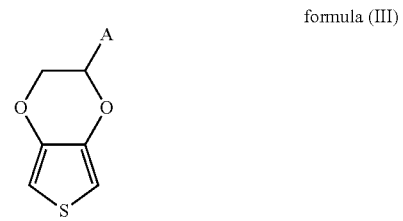

formula (III)

wherein in formula (III), A may be an antifouling molecule group.

The second monomer 104B also may be a derivative of 3,4-ethylenedioxythiophene (EDOT). In some embodiments, the second monomer 104B may be a derivative of 3,4-ethylenedioxythiophene (EDOT) and have an antifouling molecule group. Specifically, A may be a group having zwitterionic properties. In accordance with some embodiments, A may be betaine, amino acid, peptide, a polymer of 2-hydroxyethyl methacrylate (HEMA) or a derivative thereof, polyethylene glycol or an oligomer thereof (PEG or OEG), hydroxyl group, or a combination thereof.

In some embodiments, the betaine may include, but is not limited to, phosphobetaine (PB), sulfobetaine (SB), carboxybetaine (CB), or a combination thereof. In some embodiments, the amino acid may include, but is not limited to, cysteine (Cys), aspartic acid (Asp), glutamic acid (Glu), lysine (Lys), or a combination thereof. In some embodiments, the peptide may include 1 to 20 amino acids or 1 to 12 amino acids. In some embodiments, the structure of the peptide may include Asp-Cys, Glu-Cys, Cys-Lys, Cys-Lys-Cys-Lys, or a combination thereof, but it is not limited thereto.

In addition, as shown in FIG. 2C, In accordance with some embodiments, the monomer composition may include the third monomer 104C as shown in formula (IV),

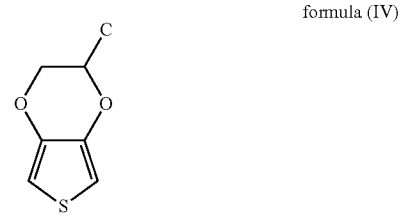

formula (IV)

wherein in formula (IV), C may be -L-E, wherein L may be a second linking group, and E may be an enzyme unit.

The third monomer 104C also may be a derivative of 3,4-ethylenedioxythiophene (EDOT). In some embodiments, the third monomer 104C may be a derivative of 3,4-ethylenedioxythiophene (EDOT) and have an enzyme group that can be connected to or form a bond with 3,4-ethylenedioxythiophene. The enzyme unit may be connected to 3,4-ethylenedioxythiophene through the second linking group. The second linking group may be a group capable of forming a chemical bond with the enzyme to achieve the purpose of fixing the enzyme. In accordance with some embodiments, the second linking group may include a derivative of carbonyl or carboxylic acid. For example, in some embodiments, the second linking group may include, but is not limited to, maleimide (MI), acrylate, methacrylate, or a combination thereof.

In some embodiments, the enzyme unit may include, but is not limited to, glucose oxidase, glucose dehydrogenase, pyrroloquinoline quinine glucose dehydrogenase A (PQQGDH-A), pyrroquinoline quinone glucose dehydrogenase B (PQQGDH-B), NAD (P)-dependent glutamate dehydrogenase (NAD(P)-GDH), FAD-dependent glutamate dehydrogenase (FADGDH), uricase, urate oxidase, cholesterol oxidase, sulfur-containing enzyme, or a combination thereof. In some other embodiments, an enzyme unit having a suitable function may be selected according to the purpose of the polymer film 104.

In accordance with some embodiments, the molar ratios of the first monomer 104A, the second monomer 104B, and the third monomer 104C may be in a range from 98:1:1 to 1:1:98.

Next, as shown in FIGS. 2C and 2D, the monomer composition described above and the self-assembly monolayer 104' may be subjected to the polymerization reaction P to form the polymer film 104. Specifically, the first monomer 104A, the second monomer 104B, and the third monomer 104C may form covalent bonds with each other through the polymerization reaction P. The first monomer 104A, the second monomer 104B, and the third monomer 104C may be copolymerized with the self-assembly monolayer 104' that has been formed on the surface 102a of the conductive substrate 102 to form a copolymer film (i.e. the polymer film 104), which may be stably attached to the conductive substrate 102 and may have anti-biofouling ability and characteristics of low impedance.

In accordance with some embodiments, the molecular weight of the polymer film 104 that is formed may be in a range from about 100 to about 1000000.

In accordance with some embodiments, the polymerization reaction P may include electropolymerization, heat polymerization, photopolymerization, radical polymerization, or catalytic reaction polymerization. In some embodiments, the catalytic reaction polymerization may include an organometallic catalytic reaction polymerization. In some embodiments, when an electropolymerization reaction is used, the molecular weight of the polymer film may be adjusted by controlling the time of the electropolymerization.

It should be understood that although in the embodiments shown in FIGS. 2A to 2D, the monomer composition used to form the polymer film 104 may include three types of monomers, i.e. the first monomer 104A, the second monomer 104B, and the third monomer 104C. In some other embodiments, the composition may include only the first monomer 104A, may include only the first monomer 104A and the second monomer 104B, may include only the first monomer 104A and the third monomer 104C, or may include only the second monomer 104B and the third monomer 104C.

As described above, in accordance with some embodiments of the present disclosure, the conductive structure that is modified with the polymer film is provided. The polymer film may be formed by the polymerization of specific conductive polymer monomers based on the self-assembly monolayer (SAM). The conductive polymer film having good conductivity, anti-biofouling properties and/or enzyme sensing function.

General polymer film modification is usually applied to the surface of conductive substrates only by physical adsorption, and thus the problems such as fall off, high impedance etc. can occur easily. Unlike general polymer film modification, in accordance with some embodiments of the present disclosure, the anchor group existing in the monomer structure can bond with the surface of the conductive substrate, and then the monomer structure can be polymerized to form a conductive polymer film. The conductive polymer film that is formed has multiple anchor groups that stably bond with the conductive substrate, so that the modified conductive structure can be used for a long time, and can be used for implantable medical devices. For example, the modified conductive structure can be used for electrical stimulation medical treatment, continuous detection of enzyme electrodes and so on.

A detailed description is given in the following particular embodiments in order to provide a thorough understanding of the above and other objects, features and advantages of the present disclosure. However, the scope of the present disclosure is not intended to be limited to the particular embodiments.

Example 1: synthesis of 3,4-ethylenedioxythiophene-lipoic acid (EDOT-LA) ((2,3-dihydrothieno [3,4-b] [1,4]dioxin-2-yl)methyl 5-((R)-1,2-dithiolan-3-yl)pentanoate) (Connected by an Ester Bond)

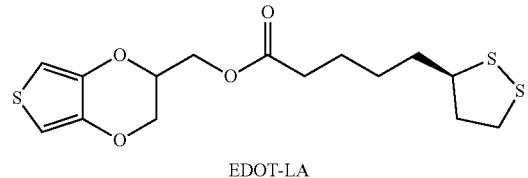 [SMILES: O=C(CCCC[C@@H]1CCSS1)OCC1COc2cscc2O1]

EDOT-LA

Hydroxymethyl EDOT (EDOT-OH) (1 eq), alpha lipoic acid (1 eq), and 4-dimethylaminopyridine (DMAP) (0.1 eq) were dissolved in a mixed solvent of dichloromethane and tetrahydrofuran (volume ratio=1:1). Next, the mixture was placed in 4° C. ice bath until all the reactants were dissolved. Then, 1.5 eq of 1-ethyl-(3-dimethylaminopropyl) carbodiimide hydrochloride (EDC-HCl) was directly added, continuously stirred and kept reacting at room temperature (about 25° C.) for 12 hours. The end of the reaction was confirmed by TLC (thin-layer chromatography), and the solvent was removed by concentration under reduced pressure. The product was then purified by silica column chromatography using methylene chloride:methane (10:1) as an eluent, and the product that was obtained was yellow oil, which was 3,4-ethylenedioxythiophene-lipoic acid (EDOT-LA).

Nuclear magnetic resonance spectroscopy was used to analyze 3,4-ethylenedioxythiophene-lipoic acid (EDOT-LA). The spectral information obtained was as follows: $^1$H NMR (400 MHz, CDCl$_3$), δ: 6.34 (d, 1H, J=4.0 Hz), 6.33 (d, 1H, J=4.0 Hz), 4.36-4.01 (m, 5H), 3.53 (m, 1H), 3.18-3.05 (m, 2H), 2.44 (m, 1H), 2.35 (t, 2H, J=8.0 Hz), 1.92-1.84 (m, 1H), 1.70-1.67 (m, 6H). $^{13}$C NMR (100 MHz, CDCl$_3$) δ:

173.2, 141.4, 141.2, 100.2, 100.1, 71.7, 65.8, 62.4, 56.4, 40.4, 38.7, 34.7, 33.9, 28.8, 24.7.

Example 2: synthesis of 3,4-ethylenedioxythiophene-aniline (EDOT-AN) ((2,3-dihydrothieno[3,4-b] [1,4]dioxin-2-yl)methyl 4-aminobenzoate) (Connected by an Ester Bond)

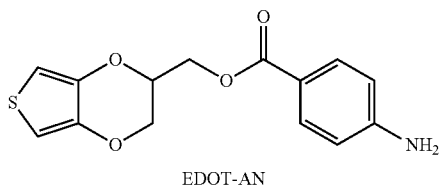 [SMILES: Nc1ccc(C(=O)OCC2COc3cscc3O2)cc1]

EDOT-AN

Hydroxymethyl EDOT (EDOT-OH) (1.0 g, 5.81 mmol), 4-amminobenzoic acid (1.2 g, 8.7 mmol), and 4-dimethylaminopyridine (DMAP) (0.36 g, 2.91 mmol) were added to a 100 mL double-necked round bottom flask and dissolved in 20 ml of anhydrous dichloromethane (DCM) and kept in an ice bath. Next, N, N'-dicyclohexylcarbodiimide (DCC) (1.8 g, 8.72 mmol) was added by two portions in 30 minutes. The mixture was stirred at room temperature for 18 hours, and the consumption rate of EDOT-OH was confirmed by TLC.

Next, water was added to dichloromethane for extraction and the organic layer was collected, extracted twice in total, and then the organic layer was filtered and concentrated under reduced pressure. The crude product was purified by silica gel column chromatography using dichloromethane: n-hexane (1:1 (v/v)) as the eluent, and the final product that was obtained was a white powder product, which was 3,4-ethylenedioxythiophene-aniline (EDOT-AN).

Nuclear magnetic resonance spectroscopy was used to analyze 3,4-ethylenedioxythiophene-aniline (EDOT-AN). The obtained spectral information was as follows: $^1$H NMR (400 MHz, CDCl$_3$) δ: 7.82 (d, 2H, J=8.5 Hz), 6.61 (d, 2H, J=8.4 Hz), 6.35 (d, 1H, J=3.6 Hz), 6.33 (d, 1H, J=3.5 Hz), 4.53-4.40 (m, 3H), 4.28 (d, 1H, J=11.6 Hz), 4.12-4.09 (m, 3H). $^{13}$C NMR (100 MHz, CDCl$_3$), δ: 166.3, 151.5, 141.6, 141.5, 132.1, 119.0, 100.2, 100.1, 72.0, 66.1, 62.4.

Example 3: synthesis of 3,4-ethylenedioxythiophene-aniline (EDOT-AN1) (N-((2,3-dihydrothieno [3,4-b] [1,4]dioxin-2-yl)methyl)-2-(4-nitrophenyl) acetamide) (Connected by Amide Bond)

Step 1

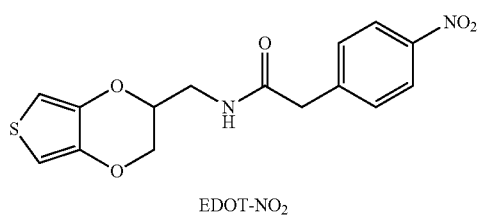 [SMILES: O=C(Cc1ccc([N+](=O)[O-])cc1)NCC1COc2cscc2O1]

EDOT-NO$_2$ p-Nitrophenylacetic acid (EDOT-NH$_2$) (0.60 g, 3.31 mmol) was added to a double-necked round bottom flask and dissolved in 50 mL of anhydrous dichloromethane. Next, the mixture was cooled in ice bath and 4-dimethylaminopyridine (DMAP) (0.20 g, 1.61 mmol) and N-hydroxysuccinimide (0.4 g, 3.63 mmol) were added, and stirred at 0° C. for 5 minutes. Cyclohexylcarbodiimide (DCC) (0.81 g, 3.95 mmol) was then added to the reactant at 0° C. Next, the reaction mixture was stirred at room temperature for 16 hours. After the reaction was ended, the reactant was filtered to remove the by-product dicyclohexyl urea (DCU), and after washed with a minimum amount of dichloromethane (DCM), the filtrate was added to EDOT-NH$_2$ (0.35 g, 1.95 mmol) and stirred at 40° C. for 24 hours.

Next, water and dichloromethane were added for extraction twice, and the organic layer was washed with 2N HCl solution and was washed with water and saline solution. The organic layer was dried over anhydrous magnesium sulfate and filtered and concentrated under reduced pressure to obtain a crude product. The crude product was purified by silica gel column chromatography to obtain a pale yellow solid product, which was an intermediate EDOT-nitro (EDOT-NO$_2$).

Step 2

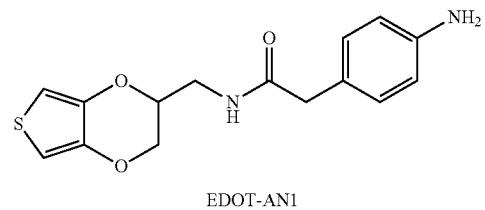 [SMILES: Nc1ccc(CC(=O)NCC2COc3cscc3O2)cc1]

EDOT-AN1

0.35 g of EDOT-nitro (1 mmol) was suspended in ethanol (20 mL), and stannous chloride (0.94 g, 4.2 mmol) was added and heated to reflux. The progress of the reaction was monitored by TLC (which shows completion of the reaction of starting material after 2 hours). Next, the reaction mixture was cooled to room temperature, 80% ethanol was distilled off under reduced pressure, and water was then added and the by-product was filtered. The filtrate was alkalized with 1N sodium hydroxide (NaOH), and then water, saline solution and dichloromethane (DCM) were used to extract the filtrate twice and wash the organic layer. Next, the reactant was dried over anhydrous magnesium sulfate and filtered. After distillation under reduced pressure, the product that was obtained was an off-white solid EDOT-amide (0.28 g, 90%), which was 3,4-ethylenedioxythiophene-aniline (EDOT-AN1) (2-(4-aminophenyl)-N-((2,3-dihydrothieno[3, 4-b] [1,4]dioxin-2-yl)methyl)acetamide).

Nuclear magnetic resonance spectroscopy was used to analyze 3,4-ethylenedioxythiophene-aniline (EDOT-AN1). The obtained spectral information was as follows: $^1$H NMR (300 MHz, CDCl$_3$) δ [ppm]: 7.02 (d, J=8.4 Hz, 2H), 6.67 (d, J=8.4 Hz, 2H), 6.31 (dd, J=10.2 Hz and J=3.6 Hz, 2H), 5.80 (bs, 1H, NH), 4.25-4.15 (m, 2H), 3.86 (dd, 1H), 3.7 (bs, 2H, NH$_2$), 3.63-3.51 (m, 1H), 3.48 (s, 2H), 3.35-3.45 (m, 1H).

Example 4: synthesis of 3,4-ethylenedioxythiophene-maleimide (EDOT-MIs) (1-((2,3-dihydrothieno[3,4-b] [1,4]dioxin-2-yl)methyl)-1H-pyrrole-2,5-dione)

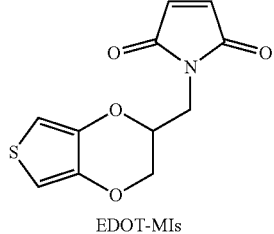 [SMILES: O=C1C=CC(=O)N1CC1COc2cscc2O1]

EDOT-MIs

Aminomethyl EDOT (EDOT-NH$_2$) (3.2 g, 18.71 mmol) was added to a 250 mL one-neck round bottom flask and dissolved with 50 mL of tetrahydrofuran, and maleic anhydride (2.0 g, 20.58 mmol) and triethylamine (2.6 ml, 20.58 mmol) were added to the mixture and stirred at room temperature for 4 hours. The tetrahydrofuran was then removed by concentration under reduced pressure. Next, the crude product was added to 20 mL of acetic anhydride, and then 1 eq of sodium acetate (1.5 g, 18.71 mmol) was added. The reactant was stirred at 65° C. for 2 hours, and the consumption rate of the raw material was confirmed by TLC. The reactant was then cooled to room temperature, and was extracted twice with water and ethyl acetate, and then washed with saline solution and dehydrated with magnesium sulfate, and filtered and concentrated under reduced pressure to obtain a crude product. The crude product was a dark liquid. The crude product was purified by silica gel column and eluted with 20% ethyl acetate:hexane, and the final product that was obtained was a pale yellow powder, which was 3,4-ethylenedioxythiophene-maleimide (EDOT-MIs).

Nuclear magnetic resonance spectroscopy was used to analyze 3,4-ethylenedioxythiophene-maleimide (EDOT-MIs). The obtained spectral information was as follows: $^1$H NMR (300 MHz, CDCl$_3$) δ [ppm]: 6.76 (s, 2H), 6.32 (2H), 4.42-4.35 (m, 1H), 4.22-4.17 (m, 1H), 3.98-3.86 (m, 2H), 3.75-3.68 (m, 2H).

Example 5: synthesis of 3,4-ethylenedioxythiophene-phosphocholine (EDOT-PC) ((2,3-dihydrothieno[3,4-b] [1,4]dioxin-2yl)methyl(2-(trimethylammonio)ethyl)phosphonate)

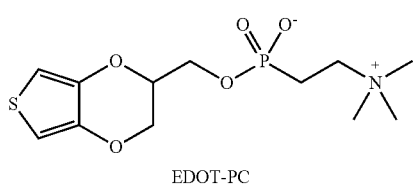

EDOT-PC

EDOT-PC was prepared by reference to the contents of the literature Nature Communication, 2014, 5, 4523.

Example 6: synthesis of 3,4-ethylenedioxythiophene-maleimide (EDOT-MI) (2-((2,3-dihydrothieno[3,4-b] [1,4]dioxin-2-yl)methoxy)-N-(2-(2,5-dioxo-2,5-dihydro-1H-pyrrol-1-yl)ethyl)acetamide)

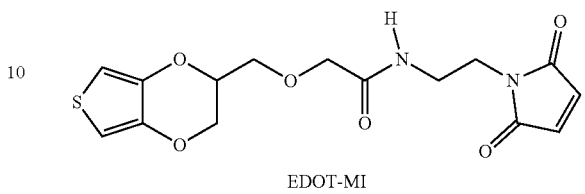

EDOT-MI

EDOT-MI was prepared by reference to the contents of the literature Nature Communication, 2014, 5, 4523.

Example 7: Preparation of a Self-Assembly Monolayer (EDOT-LA SAM) Between EDOT-LA and a Gold Electrode The gold electrode was washed with a cleaning solution (the volume ratio of deionized water:ammonia:hydrogen peroxide was 4:1:1) at 80° C. to remove organic contaminants and impurity particles on the electrode surface. Specifically, the following two methods can be used: (a) immerse the gold thin film in the cleaning solution for 30 seconds, or (b) immerse the gold-plated wafer in the cleaning solution for 10 minutes and rinse and clean the wafer three times using methanol.

10 mM EDOT-LA (prepared in Example 1, molecular weight MW=360.50 g/mol) was prepared in methanol and stirred overnight to assist in dissolving the EDOT-LA. Next, the gold electrode was immersed in the 10 mM EDOT for 18 hours in a closed container to obtain a gold electrode that is modified with the self-assembly monolayer. Thereafter, the modified gold electrode was washed with methanol and acetonitrile, and dried at room temperature.

Example 8: Preparation of a Self-Assembly Monolayer (EDOT-LA SAM) Between EDOT-LA and a Platinum Electrode The preparation method of Example 8 was substantially the same as that of Example 7, except that the electrode used was changed to a platinum electrode.

Example 9: Preparation of a Self-Assembly Monolayer (EDOT-AN SAM) Between EDOT-AN and a Platinum Electrode 11 mmol EDOT-AN (prepared in Example 2) monomer solution was prepared in deionized water, and the EDOT-AN monomer solution was continuously stirred and maintained at 0° C. for 10 minutes. 0.1 mol sodium nitrite (NaNO$_2$) solution was prepared in 1N hydrochloric acid (HCl), and the sodium nitrite solution was added the EDOT-AN monomer solution in an ice bath, and continuously stirred at 0° C. for 10 minutes to produce a diazonium salt (diazonium salt), and the color of the mixed solution began to change. After filtration, the solution was electrochemically reduced on a platinum-plated quartz crystal microbalance (QCM) wafer, and the voltage of cyclic voltammetry was from −0.6 V to 0.2 V. The platinum plate was then washed with deionized water and dried.

Example 10: Electropolymerization of a Gold Electrode Modified with an Antifouling Molecule Group (PEDOT-PC)

The electrolyte for the polymerization reaction was as follows: 0.1M lithium perchlorate (LiClO$_4$) and 0.05M sodium trimethylsilylpropylsulfonate (DSS) were dissolved in acetonitrile. The LiClO$_4$/DSS electrolyte was used to prepare a monomer solution of EDOT-PC (prepared in Example 5, the molecular weight MW=337.33 g/mol), and the solution was vibrated with ultrasound for 5 to 15 minutes to promote dissolution.

Next, an unmodified gold electrode (a gold electrode not modified by a self-assembly monolayer) that has been washed was used as the working electrode in the EDOT monomer solution, the polymerization was induced by cyclic voltammetry (−0.5 V to 1.25 V with Ag/Ag+, scan rate=0.1 volt/sec) so that the copolymer film of polymer poly(EDOT-PC) was deposited on the surface of the gold electrode. The gold electrode with poly(EDOT-PC) polymer film was washed with acetonitrile at least three times, and then stored at 4° C. in the dark.

Example 11: Electropolymerization of a Gold Electrode Modified with a Self-Assembly Monolayer (SAM/PEDOT-PC)

The electrolyte for the polymerization reaction was as follows: 0.1M lithium perchlorate (LiClO$_4$) and 0.05M sodium trimethylsilylpropylsulfonate (DSS) were dissolved in acetonitrile. The LiClO$_4$/DSS electrolyte was used to prepare a monomer solution of EDOT-PC (prepared in Example 5, the molecular weight MW=337.33 g/mol), and the solution was vibrated with ultrasound for 5 to 15 minutes to promote dissolution.

Next, the gold electrode modified with the self-assembly monolayer prepared in Example 7 was used as the working electrode in the EDOT monomer solution, the polymerization was induced by cyclic voltammetry (−0.5 V to 1.25 V with Ag/Ag+, scan rate=0.1 volt/sec) so that the copolymer film of polymer poly(EDOT-PC-co-EDOT-LA) was deposited on the surface of the gold electrode. The gold electrode with poly(EDOT-PC-co-EDOT-LA) polymer film was then washed with acetonitrile at least three times, and then stored at 4° C. in the dark.

Example 12: Electropolymerization of a Platinum Electrode Modified with a Self-Assembly Monolayer (SAM/PEDOT-PC)

The electrolyte for the polymerization reaction was as follows: 0.1M lithium perchlorate (LiClO$_4$) and 0.05M sodium trimethylsilylpropylsulfonate (DSS) were dissolved in acetonitrile. The LiClO$_4$/DSS electrolyte was used to prepare a monomer solution of EDOT-PC (prepared in Example 5, the molecular weight MW=337.33 g/mol), and the solution was vibrated with ultrasound for 5 to 15 minutes to promote dissolution.

Next, the platinum electrode modified by the self-assembly monolayer prepared in Example 8 was used as the working electrode in the EDOT monomer solution, the polymerization was induced by cyclic voltammetry (−0.5 V to 1.25 V with Ag/Ag+, scan rate=0.1 volt/sec) so that the copolymer film of polymer Poly(EDOT-PC-co-EDOT-LA) was deposited on the surface of the platinum electrode. The platinum electrode with poly(EDOT-PC-co-EDOT-LA) polymer film was then washed with acetonitrile at least three times, and then stored at 4° C. in the dark.

Example 13: Electropolymerization of a Platinum Electrode Modified with a Self-Assembly Monolayer (SAM/PEDOT-PC)

0.1 mol of lithium perchlorate (LiClO$_4$) and 50 mmol of sodium succinooctyl sulfonate (DSS) were dissolved in acetonitrile. The electrolyte was used to prepare a copolymer solution: EDOT-PC (10 mmol) (prepared in Example 5, the molecular weight MW=337.33 g/mol): EDOT-OH (10 mmol) (brand: Sigma Aldrich), and the solution was vibrated with ultrasound for 5 to 15 minutes to promote dissolution.

Next, the platinum electrode modified with the self-assembly monolayer prepared in Example 9 was used as the working electrode in the EDOT monomer solution, the polymerization was induced by cyclic voltammetry (−0.5 V to 1.25 V, scan rate=0.1 volt/sec) so that the copolymer film of polymer poly(EDOT-AN-co-EDOT-PC-co-EDOT-OH) was deposited on the surface of the platinum electrode. The platinum electrode with poly(EDOT-AN-co-EDOT-PC-co-EDOT-OH) polymer film was then washed with acetonitrile at least three times, and then stored at 4° C. in the dark.

Example 14: Preparation of an Enzyme-Modified Gold Electrode (PEDOT-MI-GOX)

The gold electrode (0.15 cm×1 cm) was washed with a cleaning solution (the volume ratio of deionized water: hydrogen peroxide solution was 3:1) at 80° C. for 8 minutes to remove organic pollutants and impurity particles on the electrode surface. The gold electrode was then rinsed with deionized water and methanol three times. Next, 10 mM EDOT-LA was prepared in methanol, and was vibrated with ultrasound until dissolved. The gold electrode was immersed in the 10 mM EDOT-LA for 24 hours in a closed container to obtain a gold electrode that is modified with the self-assembly monolayer. Thereafter, the modified gold electrode was washed with methanol and acetonitrile, and dried with nitrogen.

The electrolyte for the polymerization reaction was as follows: 0.1M lithium perchlorate (LiClO$_4$) and 0.05M sodium trimethylsilyl propylsulfonate (DSS) were dissolved in acetonitrile. The electrolyte was used to prepare a monomer solution of EDOT-MI (prepared in Example 6), and the solution was vibrated with ultrasound for 5 to 15 minutes to promote dissolution, and then filtered by a 0.45 μm PVDF filter membrane.

The gold electrode modified with the self-assembly monolayer was used as the working electrode in EDOT monomer solution, the polymerization was induced by cyclic voltammetry (−0.6 V to 1.1 V with Ag/Ag+, scan rate=0.1 volt/sec) so that the copolymer film of polymer poly(EDOT-MI-co-EDOT-LA) was deposited on the surface of the gold electrode. The gold electrode with poly(EDOT-MI-co-EDOT-LA) polymer film was then washed with acetonitrile at least three times, and then stored at room temperature in the dark.

Next, 50 μM glucose oxidase (GOX) (brand: SIGMA, catalogue number: G2133-50KU) was prepared. The polymerized poly(EDOT-MI-co-EDOT-LA) gold electrode was immersed in the 50 μM glucose oxidase, reacted at room temperature for 12 hours to form poly(EDOT-MI-co-EDOT- LA-co-EDOT-GOX), and then it was taken out and washed three times with PBS (phosphate buffered saline) and stored in PBS (pH 7.0) at 4° C.

Example 15: Preparation of an Enzyme-Modified Platinum Electrode (PEDOT-MI-GOX)

The preparation method of Example 15 was substantially the same as that of Example 14, except that the electrode used was changed to a platinum electrode.

Example 16: Preparation of an Enzyme-Modified Gold Electrode (PEDOT-PC-MI-GOX) (PC:MI/1:1)

The gold electrode (0.15 cm×1 cm) was washed with a cleaning solution (the volume ratio of deionized water: hydrogen peroxide was 3:1) at 80° C. for 8 minutes to remove organic pollutants and impurity particles on the electrode surface. The gold electrode was then rinsed with deionized water and methanol three times. Next, 10 mM EDOT-LA was prepared in methanol, and was vibrated with ultrasound until dissolved. The gold electrode was immersed in the 10 mM EDOT-LA for 24 hours in a closed container to obtain a gold electrode that is modified with the self-assembly monolayer. Thereafter, the modified gold electrode was washed with methanol and acetonitrile, and dried with nitrogen.

The electrolyte for the polymerization reaction was as follows: 0.1M lithium perchlorate ($LiClO_4$) and 0.05M sodium trimethylsilyl propylsulfonate (DSS) were dissolved in acetonitrile. The electrolyte was used to prepare a monomer solution of 10 mM EDOT-PC-MI (PC:MI/1:1), and the solution was vibrated with ultrasound for 5 to 15 minutes to promote dissolution, and then filtered by a 0.45 μm PVDF filter membrane.

The gold electrode modified with the self-assembly monolayer was used as the working electrode in EDOT monomer solution, the polymerization was induced by cyclic voltammetry (−0.6 V to 1.1 V with Ag/Ag+, scan rate=0.1 volt/sec) so that the polymer poly(EDOT-MI-co-EDOT-LA) film was deposited on the surface of the gold electrode. The gold electrode with poly(EDOT-MI-co-EDOT-LA) polymer film was then washed with acetonitrile at least three times, and then stored at room temperature in the dark.

Next, 50 μM glucose oxidase (GOX) (brand: SIGMA, catalogue number: G2133-50KU) was prepared. The polymerized poly(EDOT-MI-co-EDOT-LA) gold electrode was immersed in the 50 μM glucose oxidase, reacted at room temperature for 12 hours to form PEDOT-PC-MI-GOX, and then it was taken out and washed three times with PBS and stored in PBS (pH 7.0) at 4° C.

Example 17: Preparation of an Enzyme-Modified Platinum Electrode (PEDOT-PC-MI-GOX) (PC:MI/1:1)

The preparation method of Example 17 was substantially the same as that of Example 16, except that the electrode used was changed to a platinum electrode.

Example 18: Preparation of an Enzyme-Modified Gold Electrode (PEDOT-PC-MI-GOX) (PC:MI/1:4)

The gold electrode (0.15 cm×1 cm) was washed with a cleaning solution (the volume ratio of deionized water: hydrogen peroxide was 3:1) at 80° C. for 8 minutes to remove organic pollutants and impurity particles on the electrode surface. The gold electrode was then rinsed with deionized water and methanol three times. Next, 10 mM EDOT-LA was prepared in methanol, and was vibrated with ultrasound until dissolved. The gold electrode was immersed in the 10 mM EDOT-LA for 24 hours in a closed container to obtain a gold electrode that is modified with the self-assembly monolayer. Thereafter, the modified gold electrode was washed with methanol and acetonitrile, and dried with nitrogen.

The electrolyte for the polymerization reaction was as follows: 0.1M lithium perchlorate ($LiClO_4$) and 0.05M sodium trimethylsilyl propylsulfonate (DSS) were dissolved in acetonitrile. The electrolyte was used to prepare a monomer solution of 10 mM EDOT-PC-MI (PC:MI/1:4), and the solution was vibrated with ultrasound for 5 to 15 minutes to promote dissolution, and then filtered by a 0.45 μm PVDF filter membrane.

The gold electrode modified with the self-assembly monolayer was used as the working electrode in EDOT monomer solution, the polymerization was induced by cyclic voltammetry (−0.6 V to 1.1 V with Ag/Ag+, scan rate=0.1 volt/sec) so that the polymer poly(EDOT-MI-co-EDOT-LA) film was deposited on the surface of the gold electrode. The gold electrode with poly(EDOT-MI-co-EDOT-LA) polymer film was then washed with acetonitrile at least three times, and then stored at room temperature in the dark.

Next, 50 μM glucose oxidase (GOX) (brand: SIGMA, catalogue number: G2133-50KU) was prepared. The polymerized poly(EDOT-MI-co-EDOT-LA) gold electrode was immersed in the 50 μM glucose oxidase, reacted at room temperature for 12 hours to form PEDOT-PC-MI-GOX, and then it was taken out and washed three times with PBS and stored in PBS (pH 7.0) at 4° C.

Example 19: Preparation of an Enzyme-Modified Platinum Electrode (PEDOT-PC-MI-GOX) (PC:MI/1:4)

The preparation method of Example 19 was substantially the same as that of Example 18, except that the electrode used was changed to a platinum electrode.

Comparative Example 1: Unmodified Gold Electrode

The gold electrode (0.15 cm×1 cm) was washed with a cleaning solution (the volume ratio of deionized water: hydrogen peroxide was 3:1) at 80° C. for 8 minutes to remove organic pollutants and impurity particles on the electrode surface. The gold electrode was then rinsed with deionized water and methanol three times.

The electrolyte for the polymerization reaction was as follows: 0.1M lithium perchlorate ($LiClO_4$) and 0.05M sodium trimethylsilyl propylsulfonate (DSS) were dissolved in acetonitrile. The electrolyte was used to prepare EDOT-PC/MI (a) 10 mM EDOT-PC-MI (PC:MI/1:1 mM) and (b) 10 mM EDOT-PC-MI (PC:MI/1:4 mM), and the solution was vibrated with ultrasound for 5 to 15 minutes to promote dissolution, and then filtered by a 0.45 μm PVDF filter membrane.

The gold electrode was used as the working electrode in EDOT monomer solution, the polymerization was induced by cyclic voltammetry (−0.6 V to 1.1 V with Ag/Ag+, scan rate=0.1 volt/sec) and reoxidation potential so that the polymer poly(EDOT-MI-co-EDOT-PC) film was deposited on the surface of the gold electrode. The gold electrode with poly(EDOT-MI-co-EDOT-PC) polymer film was then washed with acetonitrile at least three times, and then stored at room temperature in the dark. 50 μM glucose oxidase (GOX) was prepared. The polymerized poly(EDOT-MI-co-EDOT-PC) gold electrode was immersed in the 50 μM glucose oxidase, reacted at room temperature for 12 hours, and then it was taken out and washed three times with PBS and stored in PBS (pH 7.0) at 4° C.

Comparative Example 2: Unmodified Platinum Electrode

The platinum electrode (0.15 cm×1 cm) was washed with a cleaning solution (the volume ratio of deionized water: hydrogen peroxide was 3:1) at 80° C. for 8 minutes to remove organic pollutants and impurity particles on the electrode surface. The platinum electrode was then rinsed with deionized water and methanol three times.

The electrolyte for the polymerization reaction was as follows: 0.1M lithium perchlorate ($LiClO_4$) and 0.05M sodium trimethylsilyl propylsulfonate (DSS) were dissolved in acetonitrile. The electrolyte was used to prepare EDOT-PC/MI (a) 10 mM EDOT-PC-MI (PC:MI/1:1 mM) and (b) 10 mM EDOT-PC-MI (PC:MI/1:4 mM), and the solution was vibrated with ultrasound for 5 to 15 minutes to promote dissolution, and then filtered by a 0.45 μm PVDF filter membrane.

The platinum electrode was used as the working electrode in EDOT monomer solution, the polymerization was induced by cyclic voltammetry (−0.6 V to 1.1 V with Ag/Ag+, scan rate=0.1 volt/sec, 1 cycle) and reoxidation potential so that the polymer poly(EDOT-MI-co-EDOT-PC) film was deposited on the surface of the platinum electrode. The platinum electrode with poly(EDOT-MI-co-EDOT-PC) polymer film was then washed with acetonitrile at least three times, and then stored at room temperature in the dark. 50 μM glucose oxidase (GOX) was prepared. The polymerized poly(EDOT-MI-co-EDOT-PC) platinum electrode was immersed in the 50 μM glucose oxidase, reacted at room temperature for 12 hours, and then it was taken out and washed three times with PBS and stored in PBS (pH 7.0) at 4° C.

Test Example 1: Analysis of Electrochemical Characteristics

FIGS. 3A to 3D show test results of electrochemical characteristics analysis of conductive structures in some Examples and Comparative Examples of the present disclosure.

Figure 3A:
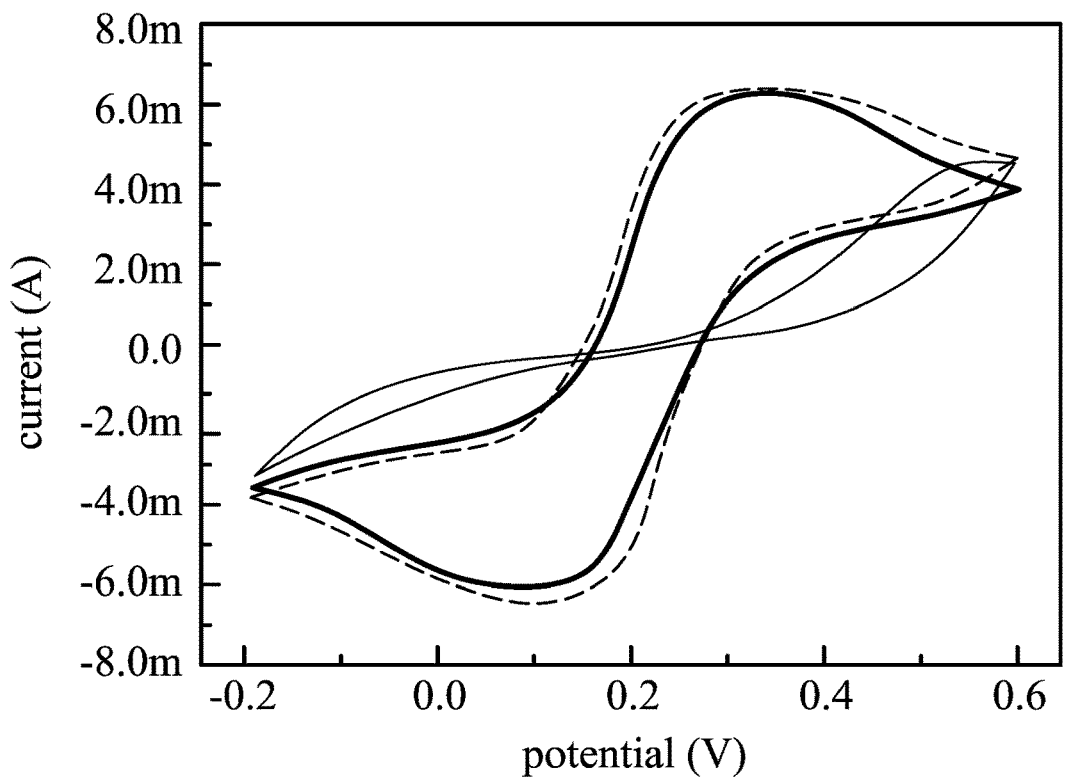
FIGS. 3A to 3D show test results of the electrochemical characteristics analysis of the conductive structures in some Examples and Comparative Examples of the present disclosure.

First, the conductive structures prepared in the above Comparative Example 1, Example 7 and Example 11 (which respectively are unmodified gold electrode, EDOT-LA SAM modified gold electrode (not yet polymerized), and SAM/PEDOT-PC modified gold electrode) were tested by cyclic voltammetry (the electrolyte used was PBS solution of Fe$(CN)_6^{3-/4-}$, wherein $Fe(CN)_6^{3-}/Fe(CN)_6^{4-}$ was 1.25 mM/1.25 mM) and the results are shown in FIG. 3A.

According to the results shown in FIG. 3A, it can be seen that the unmodified gold electrode (Comparative Example 1) had good conductivity; and the gold electrode modified only with the self-assembly monolayer but has not yet been subjected to electropolymerization (Example 7) had increased impedance and decreased conductivity decreases. As for the gold electrode modified with a polymer film (i.e. the polymer film formed by modification of the self-assembly monolayer and polymerization with EDOT monomers) (Example 11), the conductivity was substantially similar to that of the unmodified gold electrode.

Figure 3B:
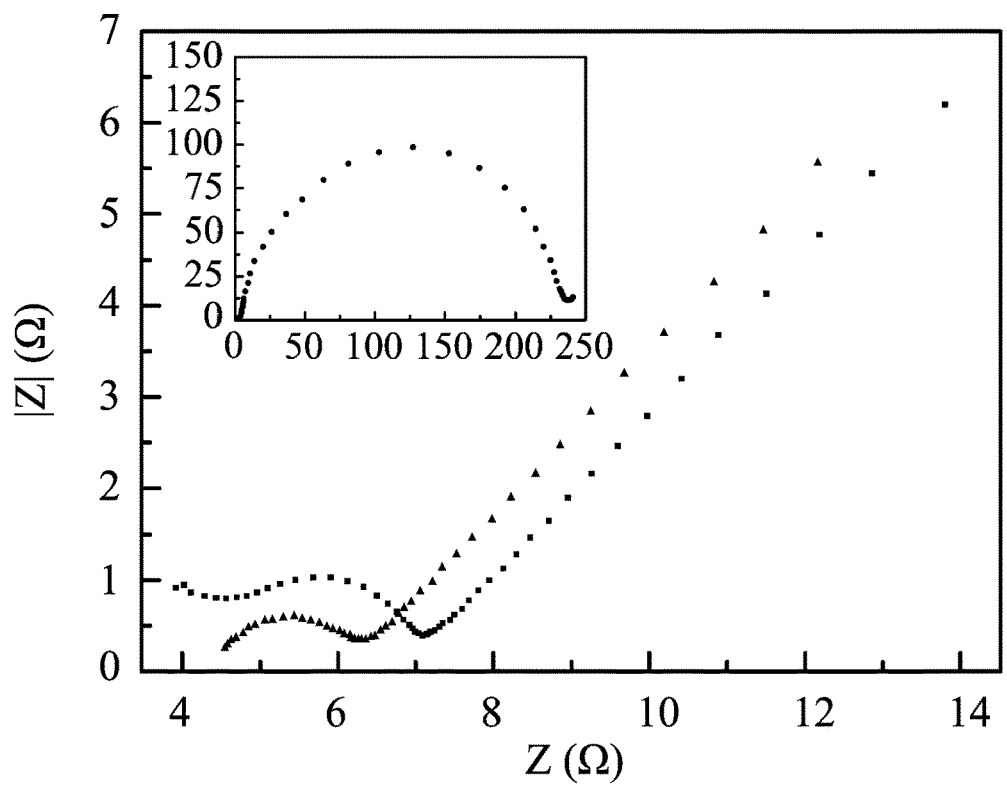

Next, the conductive structures prepared in the above Comparative Example 1, Example 7 and Example 11 (which respectively are unmodified gold electrode, EDOT-LA SAM modified gold electrode (not yet polymerized), and SAM/PEDOT-PC modified gold electrode) were tested by AC impedance test (the electrolyte used was PBS solution of $Fe(CN)_6^{3-/4-}$, wherein $Fe(CN)_6^{3-}/Fe(CN)_6^{4-}$ is 1.25 mM/1.25 mM), and the results are shown in FIG. 3B.

According to the results shown in FIG. 3B, it can be seen that the unmodified gold electrode (Comparative Example 1) had a small impedance (small semicircle diameter in the figure) and had good conductivity; and the impedance of the gold electrode modified only with the self-assembly monolayer but has not yet been subjected to electropolymerization (Example 7) became quite large. As for the gold electrode modified with the polymer film (Example 11), the impedance was similar to that of the unmodified gold electrode, and was even lower than that of the unmodified gold electrode.

Next, the conductive structures prepared in the above Comparative Example 1, Example 7 and Example 11 (which respectively are unmodified gold electrode, EDOT-LA SAM modified gold electrode (not yet polymerized), and SAM/PEDOT-PC modified gold electrode) were subjected to five cycles of time versus current test. The voltage was fixed (0.2V) and the change of the electrical signal was observed. The results are shown in FIG. 3C and FIG. 3D.

Figure 3C:
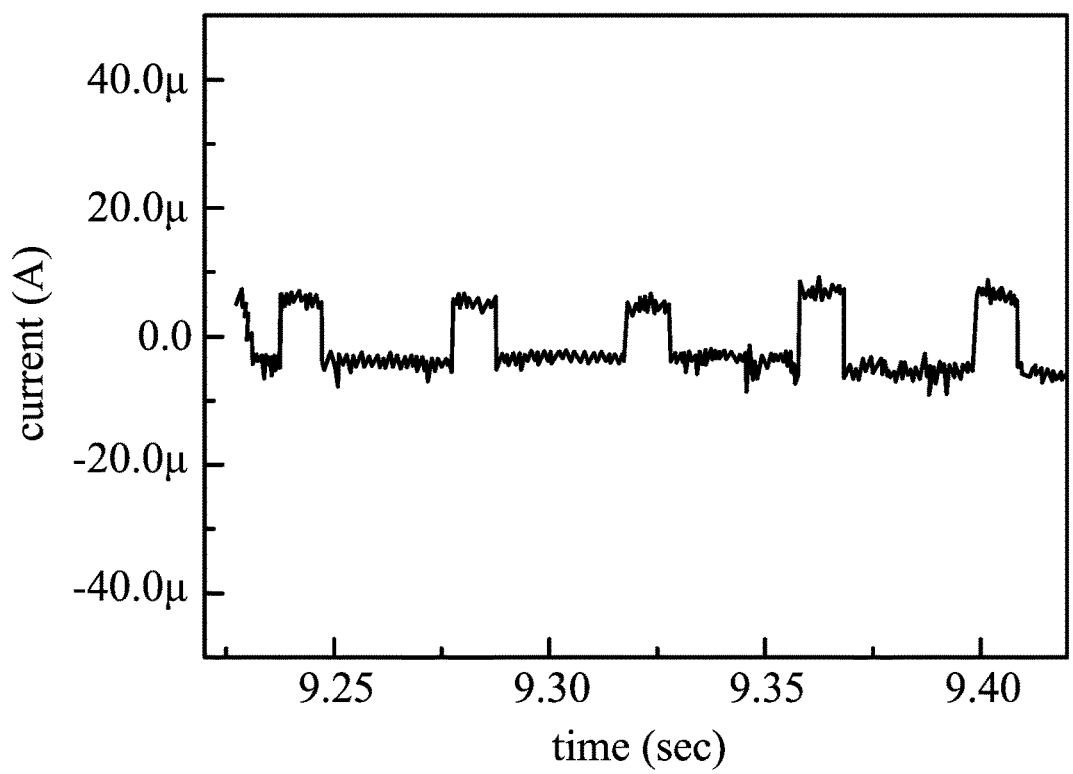
Figure 3D:
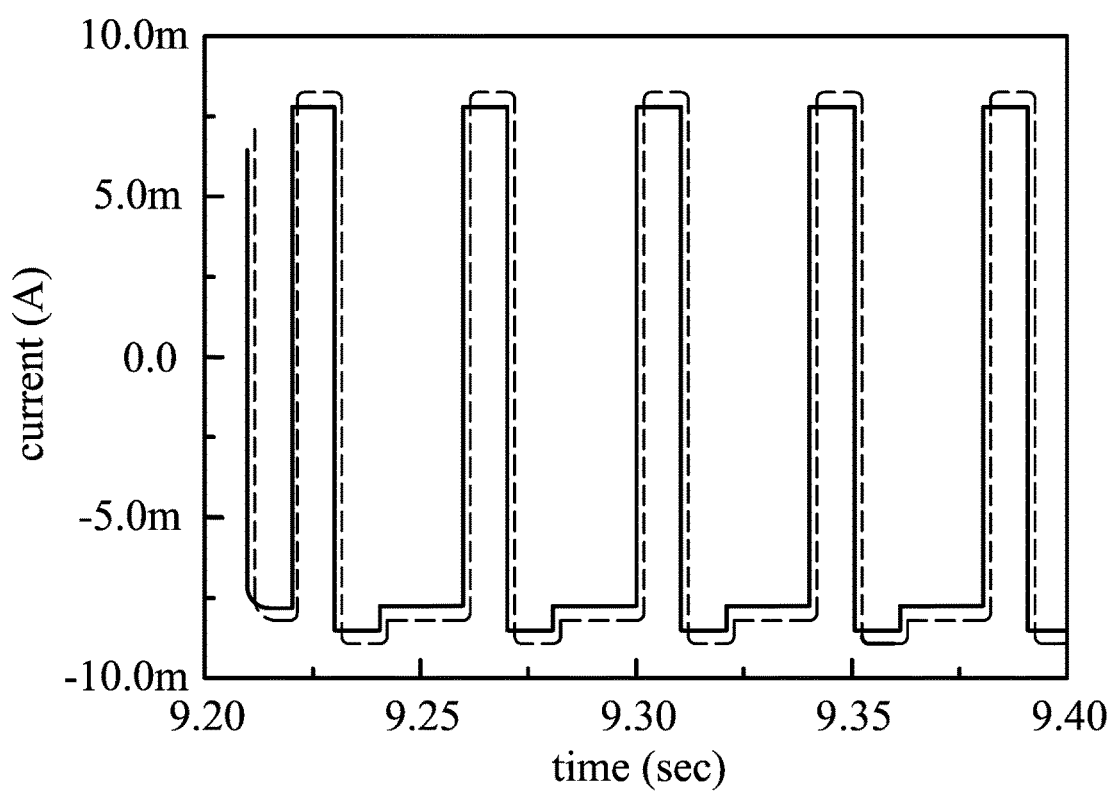

According to the results shown in FIG. 3C, it can be seen that the gold electrode modified only with the self-assembly monolayer but has not yet been subjected to electropolymerization (Example 7) had a large impedance, and thus the current was small and the difference of electrical signal was small. In addition, according to the results shown in FIG. 3D, it can be seen that the unmodified gold electrode (Comparative Example 1) had a larger current and the difference of electrical signal was large. As for the gold electrode modified with the polymer film (Example 11), the current and electrical signal were also similar to the that of the unmodified gold electrode (Comparative Example 1). Moreover, the range of current generated in Example 11 was about ±8 mA, which is within the range of the current that a general human body can withstand.

Test Example 2: Stability Test—Measurement of Contact Angle

Figure 4C:
FIGS. 4A to 4C show test results of the contact angle of the conductive structures in some Examples and Comparative Examples of the present disclosure.
Figure 4B:
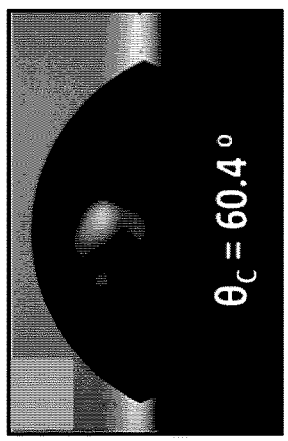
Figure 4A:
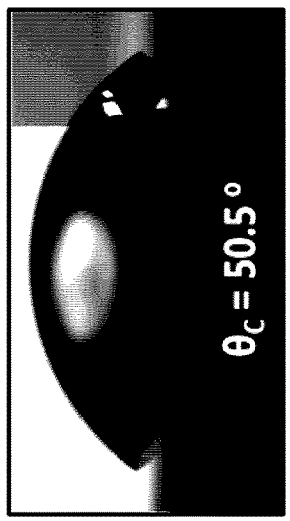

FIGS. 4A to 4C show measurement results of contact angles of the conductive structures in some Examples and Comparative Examples of the present disclosure (using the ASTM D7334 standard method). Specifically, contact angles of the water droplet formed on the conductive structures prepared in the above Comparative Example 1, Example 7 and Example 11 (which respectively are unmodified gold electrode, EDOT-LA SAM modified gold electrode (not yet polymerized), and SAM/PEDOT-PC modified gold electrode) were measured (repeating the measurement three times and obtaining an average), the results are shown in FIGS. 4A to 4C.

According to the results shown in FIGS. 4A to 4C, it can be seen that the contact angle of the unmodified gold electrode (Comparative Example 1) was about 50.5 degrees; and the contact angle of the gold electrode modified only with the self-assembly monolayer but has not yet been subjected to electropolymerization (Example 7) was about 60.4 degrees; and the contact angle of the gold electrode modified with the polymer film (Example 11) was about 13.6 degrees. Compared with gold electrodes that are not modified or only modified with self-assembly monolayer, the gold electrode modified with the polymer film had better hydrophilicity, and therefore had better anti-adhesion and antifouling properties.

Test Example 3: Stability Test—Cross-Cut Test ISO-2409

The ZTC2160 cross cut knife tool set was used to conduct film stability test of the conductive structures prepared in Example 7 and Example 12 (which respectively are EDOT-LA SAM modified gold electrode and SAM/PEDOT-PC modified platinum electrode). The peeling degree of them were compared after cutting with the knife.

First, the sample was fixed on the stable surface and ensure that the sample does not slide during the cutting process. The cutting was conducted horizontally and longitudinally (the included angle between them was 90 degrees), and every cut was 1 mm apart from each other. A total of 12 cuts were conducted (6 cuts in the longitudinal direction and 6 cuts in the horizontal direction) and 25 squares were formed after the cutting. Next, a tape (ACC753 adhesive tape) was adhered to the samples that have been cut. Specifically, the first two turns of the tape were removed and then 75 mm of the tape were removed with a steady speed and adhered to the cutting portion of the sample, and the tape was attached to the test piece by using the fingertips to gently rub the tape. The tape was removed within 5 minutes (ASTM: 90 seconds±30 seconds) and quickly removed at a steady rate (0.5 to 1 second).

The results of the Cross-cut test show that the electrodes modified with the polymer film (Example 7 and Example 12) both meet the standard of level 1 (small pieces peeled off at the intersection of the cuts, and the actual damage in the grid area was ≤5%) or level 0 (the edges of the cut were completely smooth and there was no peeling off at the edges of the grid). That is, the polymer film had good adhesion and was not easy to peel off.

Test Example 4: Anti-Adhesion Ability Test to Proteins

FIGS. 5A and 5B show test results of the anti-protein adhesion ability of the conductive structures in some Examples and Comparative Examples of the present disclosure. Specifically, the adhesion degrees of particular protein (CF 555 antibody) to the conductive structures prepared in Comparative Example 1, Example 10, Example 7 and Example 11 (which respectively are unmodified gold electrode, EDOT-PC modified gold electrode, EDOT-LA SAM modified gold electrode (not yet polymerized) and SAM/PEDOT-PC modified gold electrode) were observed.

First, the test pieces of the above conductive structures were sterilized with 70% ethanol and dried. The test pieces were washed three times with PBS, and then 4 μg/ml of CF 555 antibody (brand: Sigma-Aldrich, catalogue number: SAB4600061) was diluted in PBS by the ratio 1:500 to prepare a CF 555 antibody solution. Next, the test pieces were immersed in the CF 555 antibody solution (in PBS, 0.1 mg/ml), the CF 555 antibody solution was replaced every 7 days. After 30 days, observation was performed under a fluorescence microscope (under excitation light at 555 nm). The results are shown in FIGS. 5A and 5B.

According to the results shown in FIG. 5A, it can be seen that a large amount of protein (large amount of red fluorescent light) adhered to the unmodified gold electrode (Comparative Example 1); and almost no protein adhered to the EDOT-PC modified gold electrode (Example 10). In addition, according to the results in shown FIG. 5B, it can be seen that a large amount of protein also adhered to the gold electrode modified only with the self-assembly monolayer but has not yet been subjected to electropolymerization (Example 7); and almost no protein adhered to the gold electrode modified with the polymer film (Example 11) and it had good anti-biofouling properties.

Figure 6A:
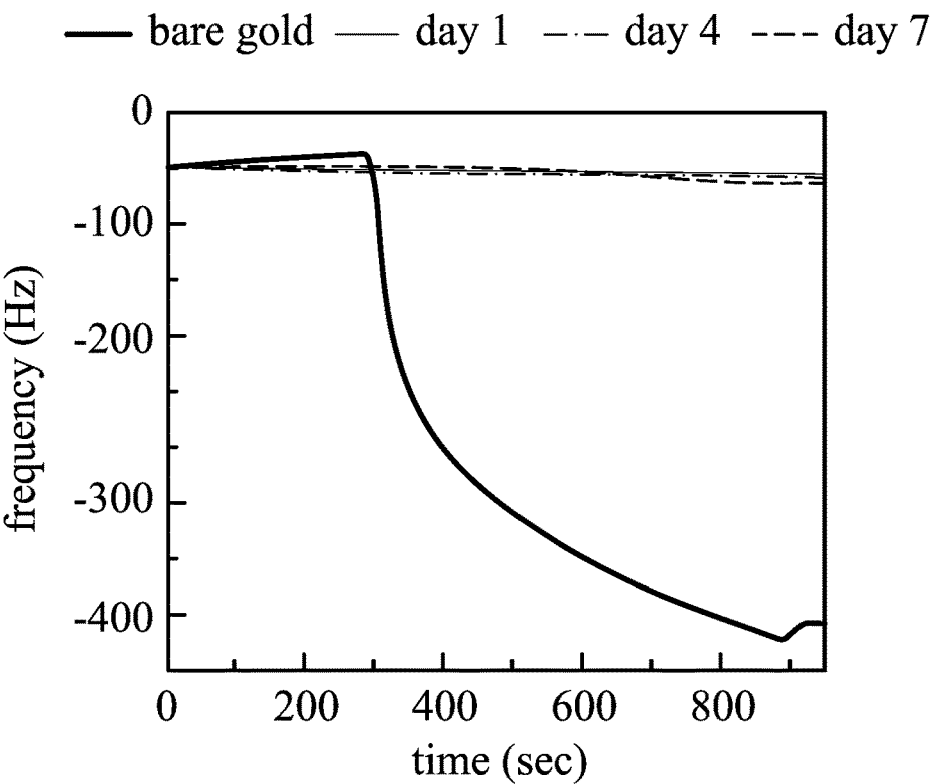
FIGS. 6A and 6B show test results of the anti-protein adhesion ability of the conductive structures in some Examples and Comparative Examples of the present disclosure.
Figure 6B:
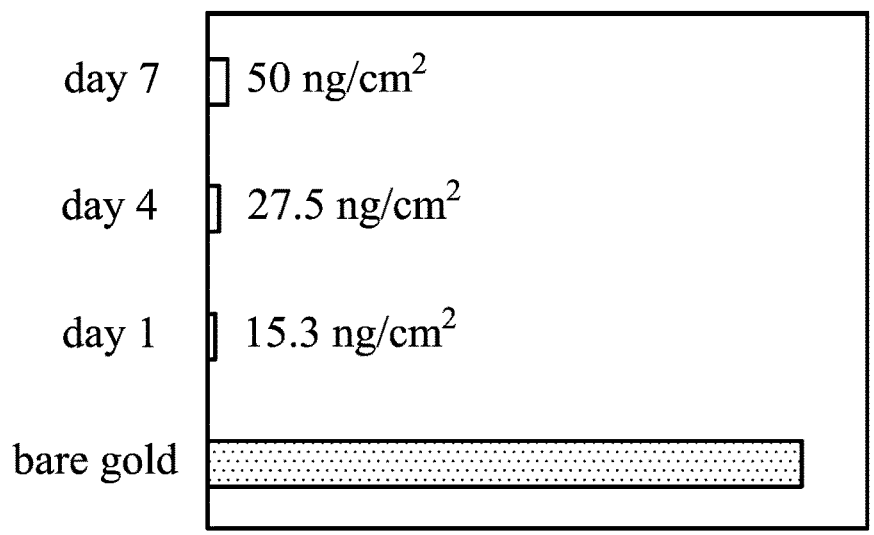

Test Example 5: Anti-Adhesion Ability Test to Nonspecific Proteins Measured by Quartz Crystal Microbalance (QCM) Method FIGS. 6A and 6B show test results of the anti-protein adhesion ability of the conductive structures in some Examples and Comparative Examples of the present disclosure, and FIG. 6B is a quantified result of FIG. 6A. Specifically, the adhesion degrees of serum protein to the conductive structures prepared in Comparative Example 1 and Example 11 (which respectively are unmodified gold electrode (bare gold) and SAM/PEDOT-PC modified gold electrode) were observed.

First, a QCM wafer sample was placed in a chamber of a QCM device (Sweden Q-sense/QCM-D analyze). The frequency of the wafer was allowed to equilibrate in the PBS solution at room temperature (flow rate: 50 μl/min), and then 10% bovine serum albumin (FBS) (Hyclone, SH30084.03) was passed through the wafer (flow rate: 50 μl/min). The wafer was then washed with PBS to wash away the physically adsorbed protein, and the value displayed represented the proteins that are adsorbed on the gold plate.

It can be seen from the results in FIGS. 6A and 6B that, compared to the unmodified gold electrode (Comparative Example 1), the adhesion degrees of the bovine serum protein on the gold electrode modified with the polymer film (Example 11) were quite low on day 7. Therefore, it is known that the polymer film also possessed good anti-adhesion ability to the serum that contains a variety of proteins.

Test Example 6: Anti-Adhesion Ability Test to Proteins

Figure 7:
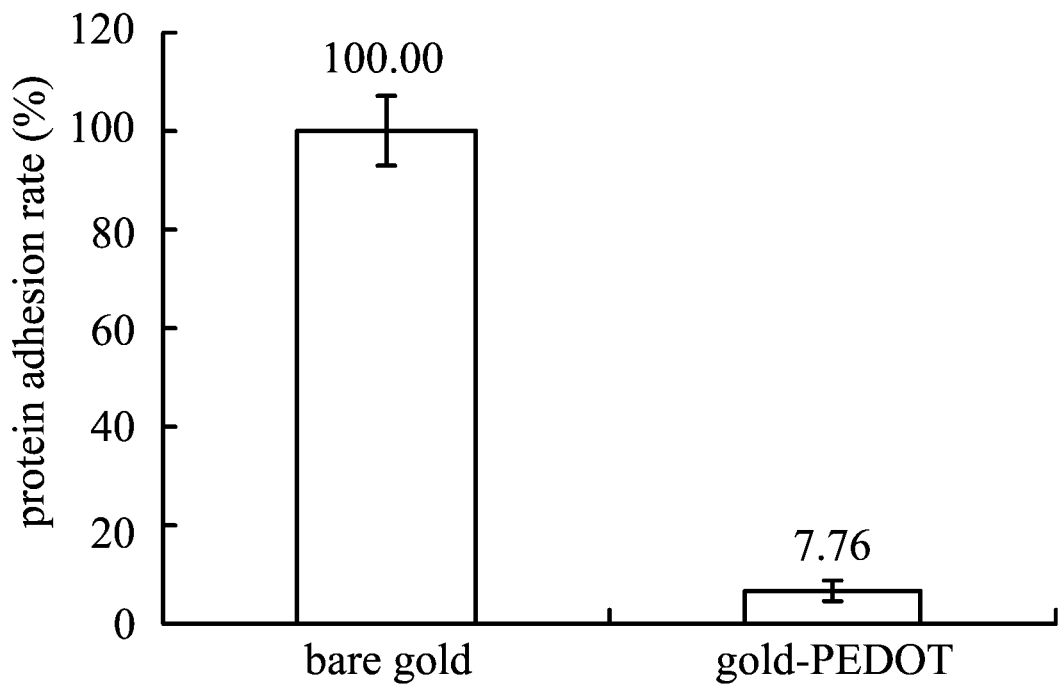
FIG. 7 shows test results of the anti-protein adhesion ability of the conductive structures in some Examples and Comparative Examples of the present disclosure.

FIG. 7 shows test results of the anti-protein adhesion ability of the conductive structures in some Examples and Comparative Examples of the present disclosure. Specifically, the adhesion degrees of fibrinogen to the conductive structures prepared in Comparative Example 1 and Example 11 (which respectively are the unmodified gold electrode (bare gold) and SAM/PEDOT-PC modified gold electrode) were observed.

First, the test pieces of the above conductive structures were immersed in 10 ug/mL fibrinogen solution (Sigma, F3879), and after reacted at 37° C. for 3 hours, the supernatant was removed and washed three times with PBST. Thereafter, a blocking buffer (Thermo Scientific, 37539) was added and reacted at 37° C. for 1 hour. Next, the test pieces were washed three times with PBST, and then a 5000-fold diluted goat anti-human fibrinogen antibody (Sigma, F8512) was added and allowed to react at 37° C. for 1 hour. Next, the test pieces were washed three times with PBST to remove unconjugated antibodies, and then a 20000-fold diluted anti-goat IgG-Peroxidase (Sigma, A5420) was added and allowed to react at 37° C. for 1 hour. Next, the test pieces were washed three times with PBST, and then the test pieces were transferred to a clean 96-well plate and TMB coloring agent (Clinical Science Products Inc., 01016-1) was added and reacted at room temperature for 5 minutes. Sulfuric acid was then added to stop the coloring reaction. 100 ul of the reaction supernatant was taken into a 96-well plate, and then an ELISA reader (Molecular Devices, Paradigm) was used to determine the optical density (O.D.) value of the reactant (the absorption wavelength used was 450 nm). The results are shown in FIG. 7. The protein adhesion rate: [(fluorescence value OD450 of sample group−fluorescence value OD450 of blank group)/(fluorescence value OD450 of control group−fluorescence value OD450 of blank group)]*100%.

It can be seen from the results of FIG. 7 that, compared to the unmodified gold electrode (left), the adhesion degree of fibrinogen to the gold electrode modified with the polymer film (right) was quite low (about 0.07 to 0.08 times the value of the unmodified gold electrode). The gold electrode modified with the polymer film had good anti-biofouling ability.

Test Example 7: Anti-Adhesion Ability Test to Proteins

Figure 8A:
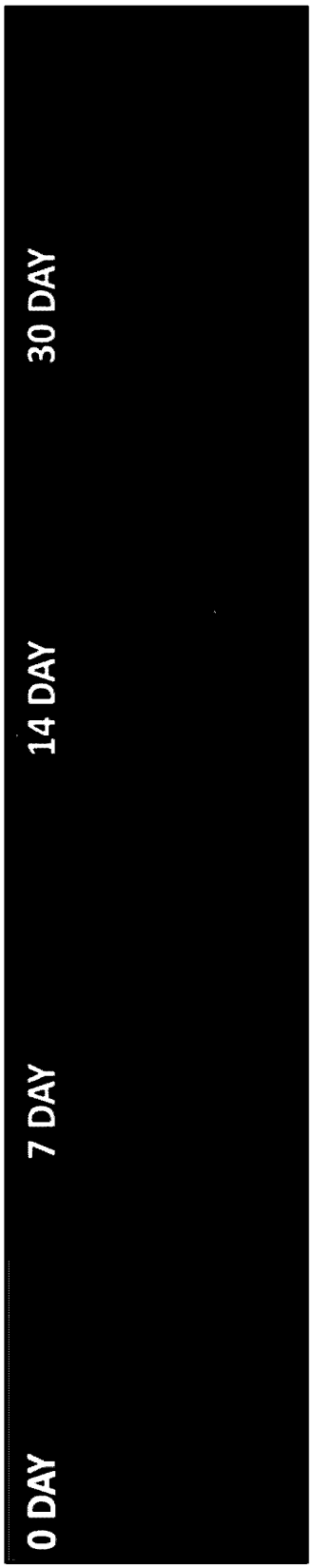
FIGS. 8A and 8B show test results of the anti-protein adhesion ability of the conductive structures in some Examples of the present disclosure.
Figure 8B:
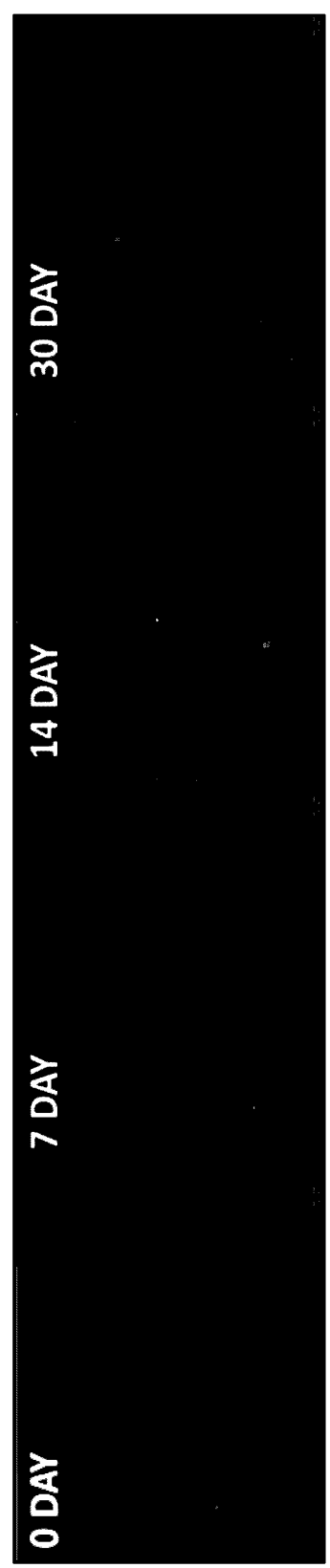

FIGS. 8A and 8B show test results of the anti-protein adhesion ability of the conductive structures in some Examples of the present disclosure. Specifically, the conductive structure prepared in Example 11 (the SAM/PEDOT-PC modified gold electrode) was used, and the adhesion degree of protein was observed. The result is shown in FIG. 8A.

Next, the conductive structure prepared in Example 10 (the gold electrode modified only with EDOT-PC) was used, and the adhesion degree of protein was observed. The result is shown in FIG. 8B.

The process of Test Example 7 was substantially similar to that of Test Example 4. FIGS. 8A and 8B further show the protein adhesion degrees of the conductive structures on day 0, day 7, 14 and 30.

According to the results shown in FIG. 8B, it can be seen that protein adhesion started to occur (red fluorescence) to the gold electrode modified only with EDOT-PC but without SAM (Example 10) on day 7, and protein adhesion became more severe after day 14. In comparison, from the results in FIG. 8A, it can be seen that only a small amount of protein adhesion occurred to the gold electrode modified with both SAM and PEDOT-PC (Example 11) on day 30. Accordingly, the polymer film modification based on the self-assembly monolayer can further improve the anti-biofouling ability.

Test Example 8: Anti-Adhesion Ability Test to Cells

Figure 9C:
FIGS. 9A to 9C show test results of the anti-cell adhesion ability of the conductive structures in some Examples and Comparative Examples of the present disclosure.
Figure 9B:
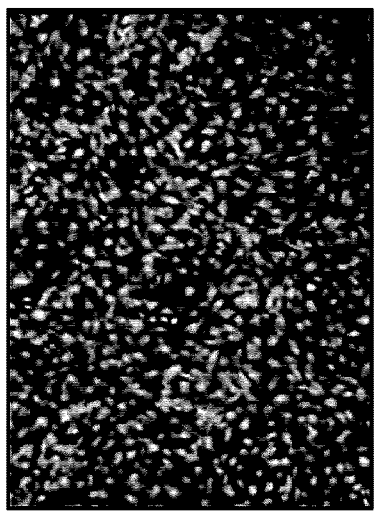
Figure 9A:
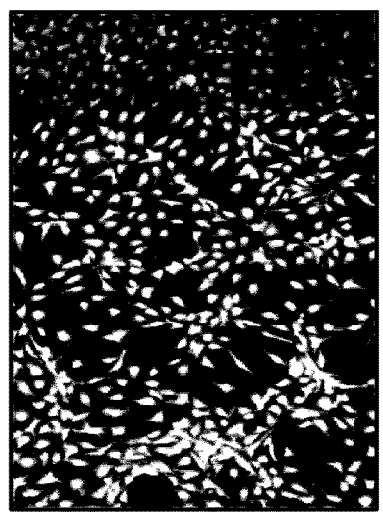

FIGS. 9A to 9C show test results of the anti-cell adhesion ability of the conductive structures in some Examples and Comparative Examples of the present disclosure. Specifically, the adhesion degrees of particular cells to the conductive structures prepared in Comparative Example 1, Example 7 and Example 11 (which respectively are unmodified gold electrode, EDOT-LA SAM modified gold electrode (not yet polymerized) and SAM/PEDOT-PC modified gold electrode) were observed.

First, the test pieces of the conductive structures were sterilized with 70% ethanol and dried. The test pieces were then washed three times with PBS, and then immersed in a DMEM medium having about 30,000 NIH3T3 cells (ATCC® CRL-1658™) and cultured at 37° C. and in the environment of 5% CO$_2$. After 3 days, the medium was removed and the test pieces were washed with PBS. Next, a live/dead cell double stain solution (5 μl of Calcein AM solution, 2.5 μl of propidium iodide solution and 2.5 ml of PBS) was prepared, and 2 ml of the live/dead cell double solution was added to the medium and was incubated at 37° C. for 15 minutes. The cells were then observed under a fluorescence microscope (under the excitation light of 485 nm), and the living cells and dead cells were monitored at the same time (green fluorescence represented adhesion of living cells; red fluorescence represented adhesion of dead cells).

As shown in FIG. 9A, a large number of living cells and some dead cells adhered to the unmodified gold electrode (Comparative Example 1) (a large amount of green fluorescence; a small amount of red fluorescence). As shown in FIG. 9B, the cell adhesion degree of the gold electrode modified only with the self-assembly monolayer but has not yet been subjected to electropolymerization (Example 7) was even more obvious. In comparison, as shown in FIG. 9C, only a small amount of cell adhesion was observed on the gold electrode modified with the polymer film (Example 11), which had better anti-biofouling ability.

Figure 10:
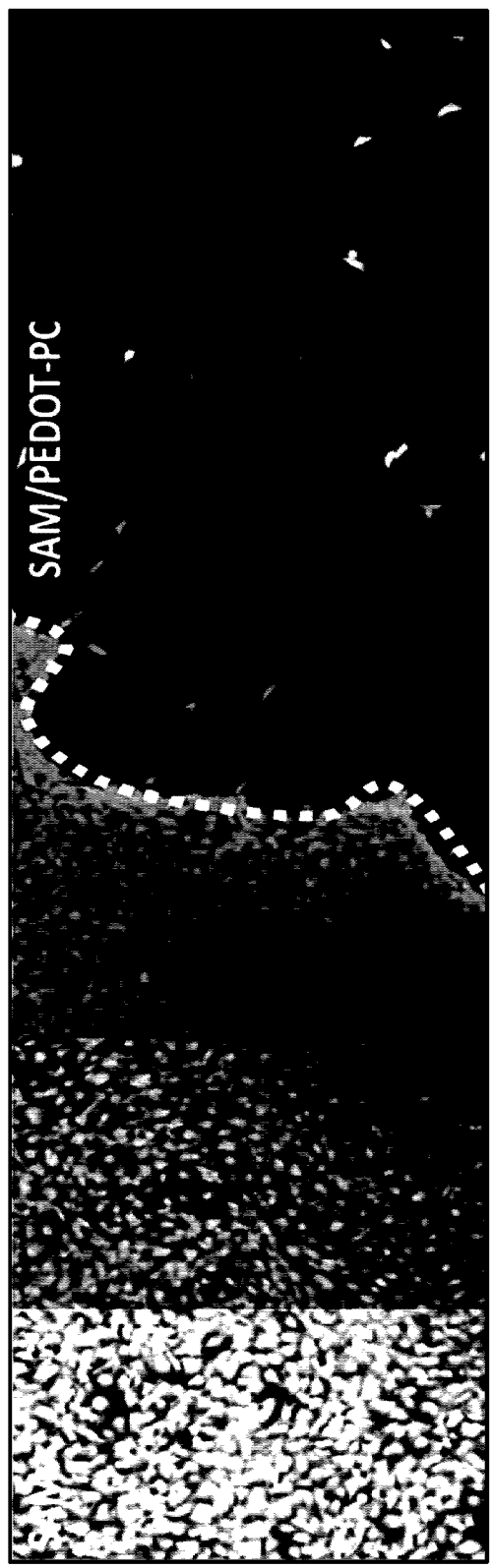
FIG. 10 shows test results of the anti-cell adhesion ability of the conductive structure in some Examples of the present disclosure.

In addition, FIG. 10 shows test results of the anti-cell adhesion ability of the conductive structure in some Examples of the present disclosure. Specifically, FIG. 10 shows the adhesion degrees of NIH3T3 cells to the conductive structures prepared in Example 8 and Example 12 (which respectively are EDOT-LA SAM modified platinum electrode (not yet polymerized) and SAM/PEDOT-PC modified platinum electrode, respectively).

According to the results shown in FIG. 10, it can be seen that a large number of living cells and some dead cells adhered to the platinum electrode modified only with the self-assembly monolayer but has not yet been subjected to electropolymerization (Example 8, the left portion of the dotted line, labeled "SAM") (a large amount of green fluorescence; a little amount of red fluorescence). In comparison, only a small amount of cell adhesion was observed on the platinum electrode modified with the polymer film (Example 12, the right portion of the dotted line, labeled "SAM/PEDOT-PC"), which had better anti-biofouling ability.

Furthermore, FIGS. 11A to 11D show test results of the anti-cell adhesion ability of the conductive structures in some Examples and Comparative Examples of the present disclosure. Specifically, the adhesion degrees of particulate cells to the conductive structures prepared in Comparative Example 2, Example 8, Example 12 and Example 14 (which respectively are unmodified platinum electrode, EDOT-LA SAM modified platinum electrode (not yet polymerized), SAM/PEDOT-PC modified platinum electrode and SAM/PEDOT-PC-co-PEDOT-OH modified platinum electrode) were observed.

As shown in FIG. 11A, a large number of living cells and some dead cells adhered to the unmodified platinum electrode (Comparative Example 2) (a large amount of green fluorescence; a small amount of red fluorescence). As shown in FIG. 11B, some live cells and dead cells also adhered to the platinum electrode modified only with the self-assembly monolayer but has not yet been subjected to electropolymerization (Example 8). In comparison, as shown in FIG. 11C, only a small amount of cell adhered to the platinum electrode modified with the polymer film (Example 12). In addition, as shown in FIG. 11D, only a small amount of cell adhesion was observed on the polymer polymerized by the monomer combination where ratio of EDOT-PC:EDOT-OH was 1:1 (Example 13). The polymer had good anti-biofouling properties.

Test Example 9: Anti-Adhesion Ability Test on Cells

Figure 12:
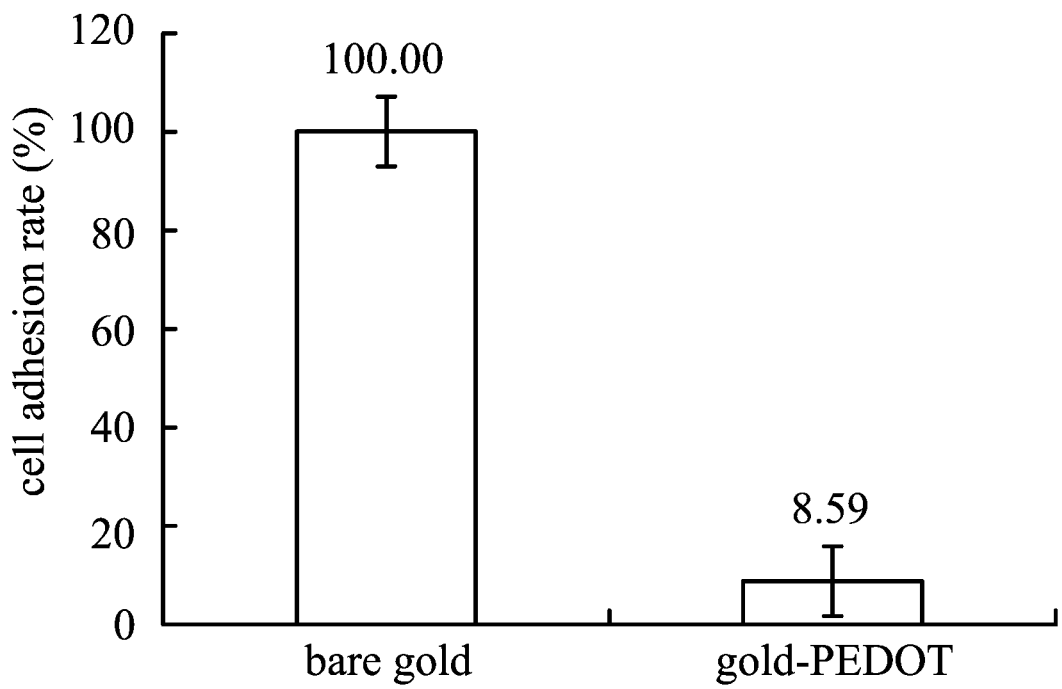
FIG. 12 shows test results of the anti-cell adhesion ability of the conductive structures in some Examples and Comparative Examples of the present disclosure.

FIG. 12 shows test results of the anti-cell adhesion ability of the conductive structures in some Examples and Comparative Examples of the present disclosure. Specifically, the adhesion degrees of particular cells to the conductive structures prepared in Comparative Example 1 and Example 11 (which respectively are the unmodified gold electrode and the SAM/PEDOT-PC modified gold electrode) were observed.

The DMEM culture solution containing 10% fetal bovine serum (Hyclone, SH30084.03) was used to culture human fibroblasts HS-68 (BCRC, 60038) and the human fibroblasts were subjected to an attachment test. In a 24-well plate, $1 \times 10^5$ cells/well of HS-68 cells were cultured with the test pieces of the above conductive structures at 37° C. and in the environment of 5% $CO_2$ for 3 hours. Next, the test pieces were washed with PBS to remove unattached cells, and transferred to another clean well containing 500 ul of cell culture solution, and PrestoBlue™ Cell Viability Reagent (Invitrogen, A13262) was used for the cell attachment test. After incubating in the environment of 37° C. and 5% $CO_2$ for 20 hours, 100 μl of the reaction supernatant were taken into a 96-well plate, and an enzyme immunoassay reader (Molecular Devices, Paradigm) was used to determine the O.D. value of the reaction solution (excitation/emission wavelength used was 535 nm/615 nm). The results are shown in FIG. 12. The cell adhesion rate: [(fluorescence value OD450 of the sample group−fluorescence value OD450 of the blank group)/(fluorescence value OD450 of the control group−fluorescence value OD450 of the blank group)]*100%.

According to the results shown in FIG. 12, it can be seen that, compared to the unmodified gold electrode (left), the adhesion of human fibroblast HS-68 to the gold electrode modified with the polymer film (right) was quite low (about 0.08 to 0.09 times the value of the unmodified gold electrode). The gold electrode modified with the polymer film had good anti-biofouling ability.

Test Example 10: Biocompatibility Test

Figure 13:
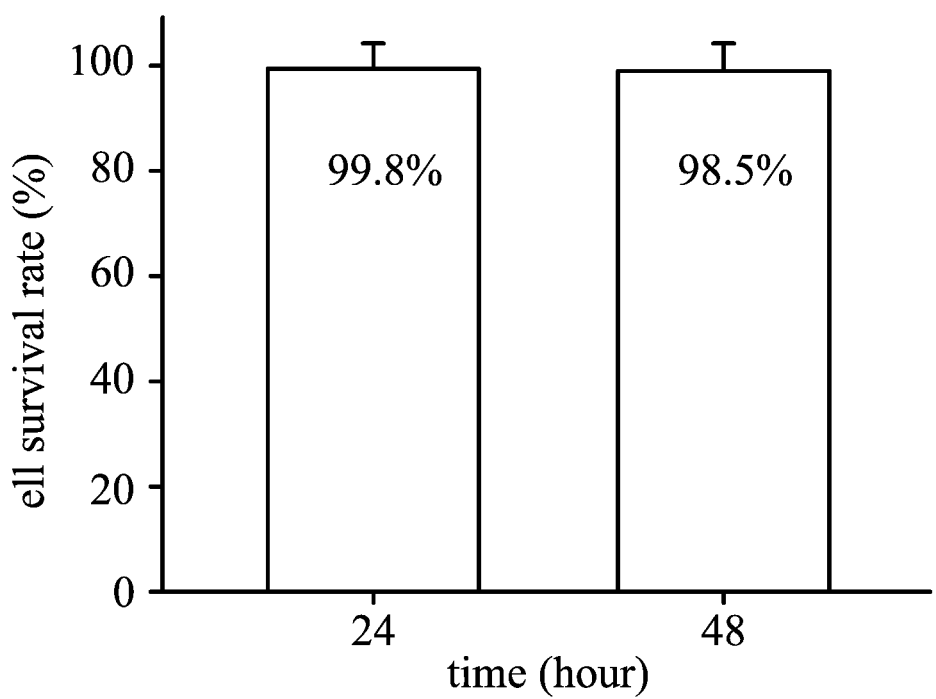
FIG. 13 shows test results of the biocompatibility of the conductive structures in some Examples of the present disclosure.

FIG. 13 shows test results of the biocompatibility of the conductive structure prepared in Example 11 (SAM/PEDOT-PC modified gold electrode) in accordance with some embodiments of the present disclosure.

L929 cells (ATCC® CCL-1™) were used for biocompatibility test. L929 cells were seeded at a density of 10,000 cells/well, and then the cells were cultured in an incubator for 24 hours (in the environment of 37° C. and 5% $CO_2$). Thereafter, 100 μl of material extraction solution (ISO10993) (component of extraction solution: MEM medium (Gibco, catalogue number: 12571071)) was added to each well, and the plate was places into an incubator for 24 hours and 48 hours (in the environment of 37° C. and 5% $CO_2$). Thereafter, the cells were taken out and the culture medium mixture in the 96-well plate was removed.

Next, 50 μl/well of MTT (3-(4,5-dimethylthiazol-2-yl)-2, 5-diphenyltetrazolium bromide) solution was added and the plate was placed into an incubator for 2 hours (in the environment of 37° C. and 5% $CO_2$). Next, 100 μl/well of DMSO was added, and the 96-well plate was placed in a shaker for 5 minutes, and the enzyme immunoassay reader was used to read the O.D. value at a wavelength of 570 nm.

The calculation of the cell survival rate is as follows: Cell survival rate (%)=(O.D. value of the experimental group/ O.D. value of the control group)×100%. The unmodified gold electrode (Comparative Example 1) was used as the control group herein.

According to the results shown in FIG. 13, it can be seen that the cells had a cell survival rate as high as 98.5% after 24 hours and 48 hours in the environment where the polymer film existed. Therefore, the polymer film had good biocompatibility.

Test Example 11: Analysis of Electrochemical Characteristics

Figure 14A:
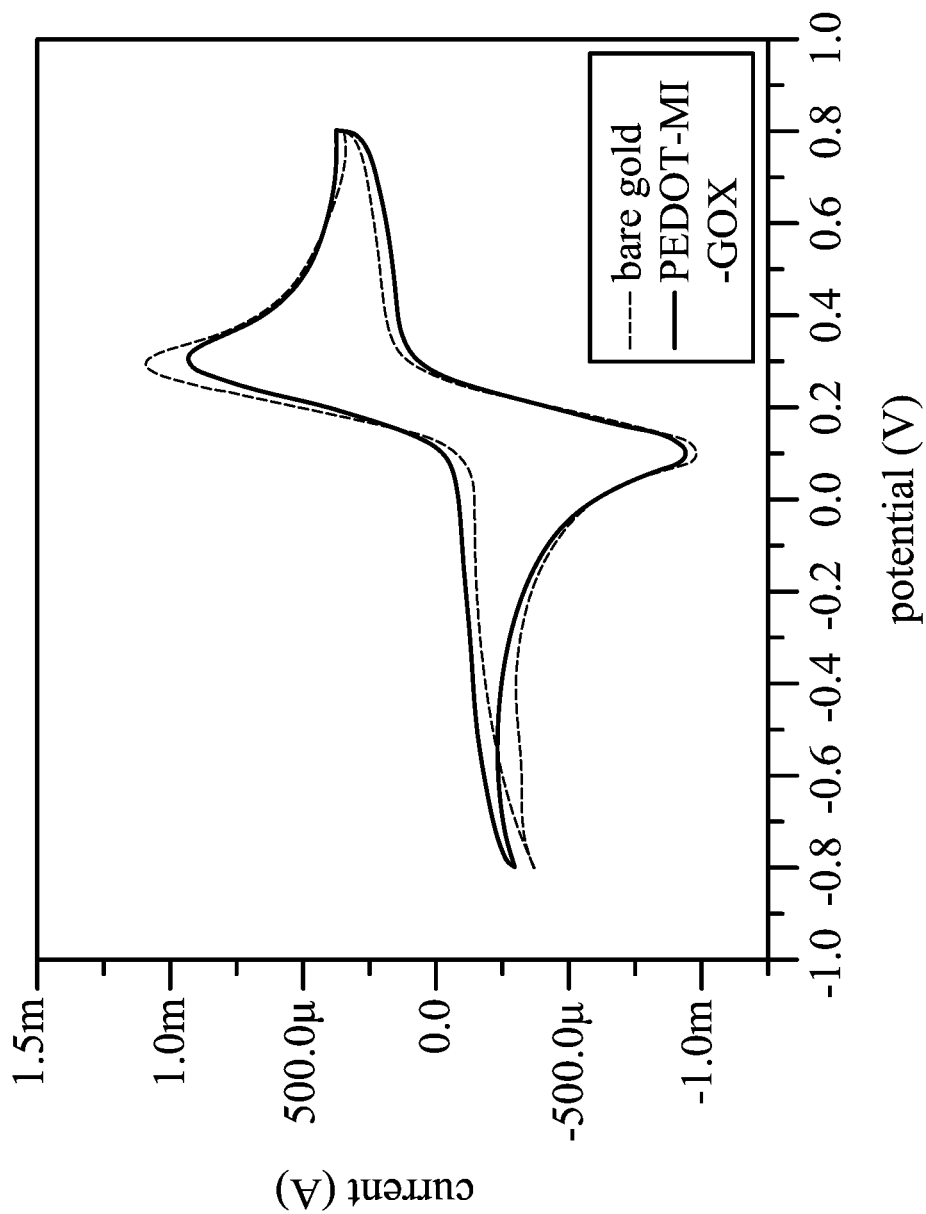
FIGS. 14A and 14B show test results of the electrochemical characteristics analysis of the conductive structures in some Examples and Comparative Examples of the present disclosure.
Figure 14B:
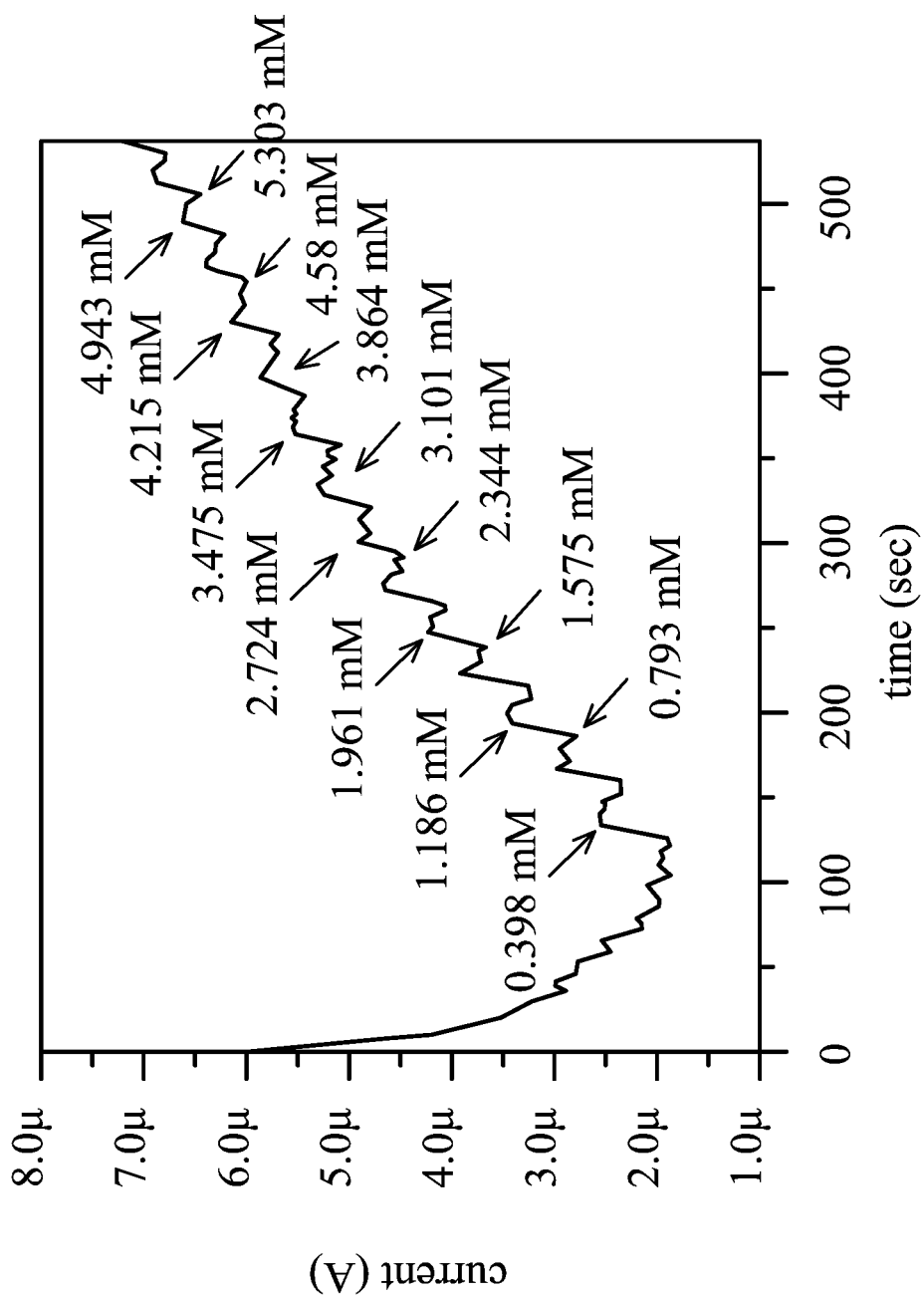
Figure 15:
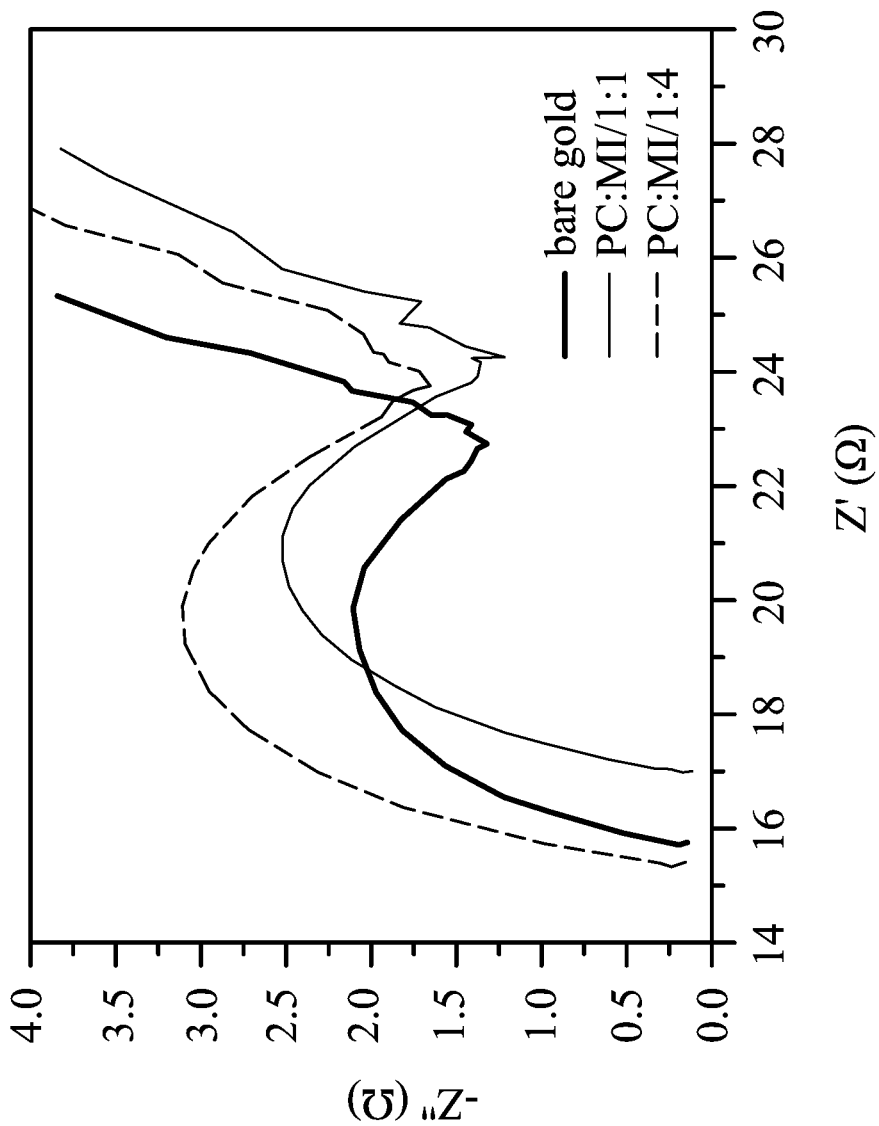
FIG. 15 shows test results of the electrochemical characteristics analysis of the conductive structures in some Examples and Comparative Examples of the present disclosure.

FIGS. 14A and 14B and FIG. 15 show test results of the electrochemical characteristics analysis of the conductive structures in some Examples and Comparative Examples of the present disclosure.

First, the conductive structures prepared in the above Comparative Example 1 and Example 14 (which respectively are unmodified gold electrode and PEDOT-MI-GOX modified gold electrode) were tested by cyclic voltammetry (the electrolyte used was PBS solution of Fe $(CN)_6^{3-/4-}$, wherein $Fe(CN)_6^{3-}/Fe(CN)_6^{4-}$ was 0.125 mM/0.125 mM). The results are shown in FIG. 14A.

According to the results shown in FIG. 14A, it can be seen that, for a gold electrode modified with the polymer film formed by the enzyme-modified monomers, its conductivity is similar to that of the unmodified gold electrode, and it had good conductivity.

Next, a sensing reaction test was performed on the conductive structure prepared in Example 14 (the electrolyte used was a PBS solution, 0.2 μL of glucose solution (100 mM) was added every 30 seconds after equilibration), and the current reaction of the PEDOT-MI GOX modified gold electrode responding to the change of glucose concentration was observed, and the results are shown in FIG. 14B.

According to the results shown in FIG. 14B, it can be seen that the conductive structure prepared in Example 14 was able to detect continuous changes of glucose concentration, and the current signal changed with the glucose concentration. That is, the polymer film formed by the enzyme-modified monomers can maintain the function of enzyme sensing and continuous detection.

In addition, the conductive structures prepared in Example 16 (PEDOT-PC:MI-GOX/1:1), Example 19 (PEDOT-PC:MI-GOX/1:4) and Comparative Example 1 were tested by AC impedance test (the electrolyte used was PBS solution of $Fe(CN)_6^{3-/4-}$, wherein $Fe(CN)_6^{3-}/Fe(CN)_6^{4-}$ is 0.125 mM/0.125 mM), and the results are shown in FIG. 15.

According to the results shown in FIG. 15, it can be seen that the unmodified gold electrode (Comparative Example 1) had a small impedance (small semicircle diameter in the figure) and has good conductivity. As for the gold electrode modified with the polymer film in which the ratio of PEDOT-PC monomer:MI-GOX monomer was 1:1 (Example 16) and the gold electrode modified with the polymer film in which the ratio of PEDOT-PC monomer:MI-GOX monomer was 1:4 (Example 19), their impedance were similar to that of the unmodified gold electrode and had good conductivity.

To summarize the above, in accordance with some embodiments of the present disclosure, the conductive structure modified with the polymer film is provided. Based on the self-assembly monolayer (SAM), the polymer film can be formed by the polymerization of specific conductive polymer monomers. In the method, a bond be formed with the surface of the conductive substrate through the anchor groups existing in the monomer structure, and then the conductive polymer film can be formed through electropolymerization of the monomers. The conductive polymer film that is formed has multiple anchor groups that are stably bonded to the conductive substrate, so that the modified conductive structure can be used for a long time. Furthermore, in accordance with some embodiments, the polymer film may be formed using the monomers having anti-biofouling properties and/or enzyme sensing function, and the conductive structure thus formed may be applied to implantable medical devices. For example, the conductive structure can be used for electrical stimulation medical treatment, continuous detection of enzyme electrodes, and so on.

Although some embodiments of the present disclosure and their advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. In addition, each claim constitutes an individual embodiment, and the claimed scope of the present disclosure also includes the combinations of the claims and embodiments. The scope of protection of present disclosure is subject to the definition of the scope of the appended claims.

What is claimed is:

1. A modified conductive structure, comprising:
   a conductive substrate; and
   a polymer film disposed over a surface of the conductive substrate, wherein a chemical bond exists between the polymer film and the conductive substrate, and the polymer film comprises repeating units as shown below:

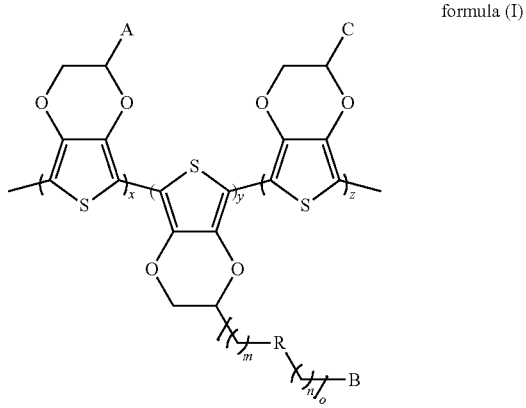

formula (I)

wherein A is an antifouling molecule group; B is 1,2-dithiolane; R is a single bond or a first linking group; C is -L-E, wherein L is a second linking group, E is an enzyme unit; x and z are each independently 0 or an integer from 1 to 10000, and y is an integer from 1 to 10000; o is 0 or an integer from 1 to 50, and when o is an integer from 1 to 50, m and n are each independently 0 or an integer from 1 to 50.

2. The modified conductive structure as claimed in claim 1, wherein the first linking group is ester, amide, thioester, ether, amine, ketone, sulfide, carbonate, carbamate, or a combination thereof.

3. The modified conductive structure as claimed in claim 1, wherein o is an integer from 1 to 50, and a plurality of R are the same or different from each other.

4. The modified conductive structure as claimed in claim 1, wherein A is betaine, amino acid, peptide, a polymer of 2-hydroxyethyl methacrylate (HEMA), polyethylene glycol, hydroxyl group, or a combination thereof.

5. The modified conductive structure as claimed in claim 4, wherein the betaine comprises phosphobetaine (PB), sulfobetaine (SB), carboxybetaine (CB), or a combination thereof.

6. The modified conductive structure as claimed in claim 4, wherein the amino acid comprises cysteine (Cys), aspartic acid (Asp), glutamic acid (Glu), lysine (Lys), or a combination thereof.

7. The modified conductive structure as claimed in claim 4, wherein the peptide comprises 1 to 20 amino acids and the structure of the peptide comprises Asp-Cys, Glu-Cys, Cys-Lys, Cys-Lys-Cys-Lys, or a combination thereof.

8. The modified conductive structure as claimed in claim 1, wherein the second linking group comprises maleimide (MI), acrylate, methacrylate, or a combination thereof.

9. The modified conductive structure as claimed in claim 1, wherein the enzyme unit comprises glucose oxidase, glucose dehydrogenase, pyrroloquinoline quinine glucose dehydrogenase A (PQQGDH-A), pytToquinoline quinone glucose dehydrogenase B (PQQGDH-B), NAD (P)-dependent glutamate dehydrogenase (NAD(P)-GDH), FAD-dependent glutamate dehydrogenase (FADGDH), uricase, urate oxidase, cholesterol oxidase, sulfur-containing enzyme, or a combination thereof.

10. The modified conductive structure as claimed in claim 1, wherein the material of the conductive substrate comprises a conductive material, a semiconductor material, or a combination thereof.

11. The modified conductive structure as claimed in claim 10, wherein the conductive substrate comprises the semiconductor material having the conductive material on a surface of the semiconductor material.

12. The modified conductive structure as claimed in claim 10, wherein the conductive material comprises gold (Au), platinum (Pt), aluminum (Al), iridium (Ir), titanium (Ti), steel, stainless steel, gold alloy, platinum alloy, platinum alloy, aluminum alloy, iridium alloy, titanium alloy, or a combination thereof.

13. The modified conductive structure as claimed in claim 10, wherein the conductive material comprises a conductive oxide, a carbon material, or a combination thereof.

14. The modified conductive structure as claimed in claim 10, wherein the semiconductor material comprises silicon (Si).

* * * * *